United States Patent
Wang et al.

(10) Patent No.: US 10,881,733 B2
(45) Date of Patent: Jan. 5, 2021

(54) BENZAMIDE AND ACTIVE COMPOUND COMPOSITIONS AND METHODS OF USE

(71) Applicant: TRANSLATIONAL DRUG DEVELOPMENT LLC, Scottsdale, AZ (US)

(72) Inventors: Tong Wang, Scottsdale, AZ (US); Stephen Gately, Scottsdale, AZ (US); Paul Gonzales, Scottsdale, AZ (US)

(73) Assignee: Translational Drug Development, LLC, Scottsdale, AZ (US)

( * ) Notice: Subject to any disclaimer, the term of this patent is extended or adjusted under 35 U.S.C. 154(b) by 279 days.

(21) Appl. No.: 15/575,340

(22) PCT Filed: May 23, 2016

(86) PCT No.: PCT/US2016/033840
§ 371 (c)(1),
(2) Date: Nov. 17, 2017

(87) PCT Pub. No.: WO2016/191397
PCT Pub. Date: Dec. 1, 2016

(65) Prior Publication Data
US 2018/0221472 A1    Aug. 9, 2018

Related U.S. Application Data

(60) Provisional application No. 62/302,781, filed on Mar. 2, 2016, provisional application No. 62/167,794, filed on May 28, 2015, provisional application No. 62/167,790, filed on May 28, 2015, provisional application No. 62/165,891, filed on May 22, 2015.

(51) Int. Cl.
| | |
|---|---|
| *A61K 39/39* | (2006.01) |
| *A61K 39/395* | (2006.01) |
| *A61K 31/4184* | (2006.01) |
| *A61K 45/06* | (2006.01) |
| *C07D 235/30* | (2006.01) |
| *C07D 401/04* | (2006.01) |
| *C07K 16/28* | (2006.01) |
| *C07D 403/04* | (2006.01) |
| *A61P 35/04* | (2006.01) |
| *A61P 35/00* | (2006.01) |
| *A61K 47/18* | (2017.01) |
| *A61K 47/22* | (2006.01) |
| *A61K 47/26* | (2006.01) |
| A61K 39/00 | (2006.01) |
| A61K 31/7068 | (2006.01) |

(52) U.S. Cl.
CPC ...... *A61K 39/3955* (2013.01); *A61K 31/4184* (2013.01); *A61K 45/06* (2013.01); *A61K 47/18* (2013.01); *A61K 47/22* (2013.01); *A61K 47/26* (2013.01); *A61P 35/00* (2018.01); *A61P 35/04* (2018.01); *C07D 235/30* (2013.01); *C07D 401/04* (2013.01); *C07D 403/04* (2013.01);

*C07K 16/2818* (2013.01); *A61K 31/7068* (2013.01); *A61K 2039/507* (2013.01); *A61K 2300/00* (2013.01); *C07K 2317/76* (2013.01)

(58) Field of Classification Search
None
See application file for complete search history.

(56) References Cited

U.S. PATENT DOCUMENTS

2014/0341902 A1    11/2014  Maecker et al.

FOREIGN PATENT DOCUMENTS

| WO | 2010151441 A1 | 12/2010 | |
|---|---|---|---|
| WO | WO 2010/151441 | * 12/2010 | ............. A01N 43/50 |
| WO | WO 2013/019906 | * 2/2013 | ............. A61P 35/00 |
| WO | 2015/048520 A1 | 4/2015 | |

OTHER PUBLICATIONS

Nie et al. (Cancer Letters, 354: 12-20, 2014).*
Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Stancovski et al. (PNAS, 88: 8691-8695, 1991).*
Jiang et al. (J. Biol. Chem., 280: 4656-4662, 2005).*
Ohaegbulam, Kim C. et al., "Human cancer immunotherapy with antibodies to the PD-1 and PD-L1 pathway", Trends in Molecular Medicine, 21(1):24-33 (Jan. 1, 2015).
Vanneman, Matthew et al., "Combining immunotherapy and targeted therapies in cancer treatment", Nature Reviews Cancer, 12(4):237-251 (Jan. 1, 2012).
Topalian, Suzanne L. et al., "Immune Checkpoint Blockade: A Common Denominator Approach to Cancer Therapy", Cancer Cell, 27(4):450-461 (Apr. 1, 2015).
Anonymous, "Anti-Human CD274 Therapeutic Antibody (AMP-224)", pp. 1-2 (May 1, 2018), Retrieved from the Internet: URL:https://www.creativebiolabs.net/pdf/TAB-116CL.pdf [retrieved on Oct. 2, 2018].

(Continued)

*Primary Examiner* — Nelson B Moseley, II
(74) *Attorney, Agent, or Firm* — Rodney J. Fuller; Booth Udall Fuller, PLC

(57) ABSTRACT

The present invention describes compositions, including pharmaceutical compositions, comprising a PD-1 axis binding antagonist, a CTLA4 antagonist, or a DNA demethylating agent and a benzamide compound and methods for use thereof, for example in the treatment of cancer. In some implementations, the methods for use including methods of treating conditions where enhanced immunogenicity is desired such as increasing tumor immunogenicity for the treatment of cancer.

17 Claims, 6 Drawing Sheets
Specification includes a Sequence Listing.

(56) References Cited

OTHER PUBLICATIONS

Masters, Gregg et al., "Antitumor Activity of Cytotoxic T-lymphocyte Antigen-4 Blockade Alone or Combined with Paclitaxel, Etoposide, or Gemcitabine in Murine Models", Journal of Immunotherapy, 32(9):994 (Oct. 31, 2009).

Robert, Caroline et al., "Ipilimumab plus Dacarbazine for Previously Untreated Metastatic Melanoma", The New England Journal of Medicine, 364(26)2517-2526 (Jun. 30, 2011).

Cooper, S. J. et al., "Reexpression of Tumor Suppressor, sFRP1, Leads to Antitumor Synergy of Combined HDAC and Methyltransferase Inhibitors in Chemoresistant Cancers", Molecular Cancer Therapeutics, 11(10):2105-2115 (Oct. 1, 2012).

Lainey, E. et al., "Azacytidine and erlotinib exert synergistic effects against acute myeloid leukemia", Oncogene, 32 (37):4331-4342 (Oct. 22, 2012).

Lu, Aijun et al., "Design, synthesis and docking studies on benzamide derivatives as histone deacetylase inhibitors", Bioorganic & Medicinal Chemistry Letters, 21(16):4924-4927 (Jun. 1, 2011).

Lu et al., "Combined PD-1 blockade and GITR triggering induce a potent antitumor immunity in murine cancer models and synergizes with chemotherapeutic drugs", Journal of Translational Medicine, 12:36 (2014).

\* cited by examiner

BENZAMIDE AND ACTIVE COMPOUND COMPOSITIONS AND METHODS OF USE

CROSS-REFERENCE TO RELATED APPLICATIONS

This application is the U.S. National Stage of International Application No. PCT/US2016/033840, filed May 23, 2016, which claims priority to U.S. Provisional Patent Application No. 62/165,891, filed May 22, 2015, U.S. Provisional Patent Application No. 62/167,790, filed May 28, 2015, U.S. Provisional Patent Application No. 62/167,794, filed May 28, 2015, and U.S. Provisional Patent Application No. 62/302,781, filed March 2, 2016, the contents of each of which are incorporated herein by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "11144_023_Seq_Listing_ST25.txt" created on May 23, 2016, and having a size of 68 kilobytes, and is filed concurrently with the specification. The sequence listing contained in this ASCII-formatted document is part of the specification and is herein incorporated by reference in its entirety.

TECHNICAL FIELD

This disclosure relates to compositions including combinations of therapeutic agents and a benzamide compound and methods of use thereof.

BACKGROUND

Cancer is the second leading cause of death in the United States. Despite new breakthroughs that have led to decreased mortality, many cancers remain refractory to treatment. Additionally, typical treatments such as chemotherapy, radiotherapy, and surgery cause a broad spectrum of undesirable side effects. In addition, many cancers often develop resistance to current chemotherapies over time. Clearly the field is in significant need of novel compounds and methods of slowing the expansion of cancer cells and that are useful in the treatment of cancer.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross-links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromatase inhibitors, bifunctional alkylating agents, etc.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

SUMMARY OF THE INVENTION

Provided are compositions, including pharmaceutical compositions, and methods for treating cancers using a composition comprising a benzamide compound, or a pharmaceutically acceptable salt or solvate thereof, and a PD-1 axis binding antagonist. The benzamide compound has a formula of

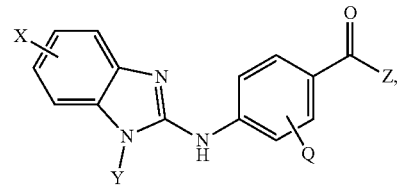

wherein: X is selected from the group consisting of H, halo, —OH, —CN, —NR'R", —OR', —SR', —OC(O)R', —NHC(O)R', —NHC(O)NR'R", —C(O)R', —NS(O)$_2$R', —S(O)$_2$NR'R", —S(O)$_2$R', guanidino, nitro, nitroso, —C$_1$-C$_6$ alkyl, aryl, —C$_3$-C$_7$ cycloalkyl, and 3 to 10-membered heterocycle, wherein the —C$_1$-C$_6$ alkyl, aryl, —C$_3$-C$_7$ cycloalkyl, or 3 to 10-membered heterocycle any of which may be unsubstituted or substituted with one or more of the following: halo, —OH, —CN, —NR'R", —OR', —SR', —OC(O)R', —NR'R", —NHC(O)R', —NHC(O)NR'R", —C(O)R', —NS(O)$_2$R', —S(O)$_2$NR'R", —S(O)$_2$R', guanidino, nitro, nitroso, —C$_1$-C$_6$ alkyl, aryl, —C$_3$-C$_7$ cycloalkyl; Y is selected from the group consisting of H, —C$_1$-C$_6$ alkyl, —C$_3$ cycloalkyl, aryl, 3 to 10-membered heterocycle wherein the —C$_1$-C$_6$ alkyl, —C$_3$-C$_{12}$ cycloalkyl, aryl, 3 to 10-membered heterocycle any of which may be unsubstituted or substituted with one or more of the following: -halo, —C$_1$-C$_6$ alkyl, —C$_3$-C$_{12}$ cycloalkyl, 3 to 10-membered heterocycle, aryl, OH, —CN, —OR', —SR', —OC(O), —NR'R", —NHC(O)R', —NHC(O)NR'R", —C(O)R', —NS(O)$_2$R', —S(O)$_2$NR'R", —S(O)$_2$R', guanidino, nitro, nitroso; R' or R" may be —H or —C$_1$-C$_6$ alkyl; Z is NHOH; and Q is selected from the group consisting of H, F, Cl, Br and I. In some embodiments, Y is selected from the group consisting of cyclopentyl, cyclohexyl, and cycloheptyl. In other embodiments, Y is selected from the group consisting of cyclopentylmethyl, cyclohexylmethyl or cycloheptylmethyl.

In some embodiments, the PD-1 axis binding antagonist is selected from the group consisting of a PD-1 binding antagonist, a PD-L1 binding antagonist, and a PD-L2 binding antagonist.

The PD-1 binding antagonist may be selected from the group consisting of an anti-PD-1 antibody, an antigen binding fragment of the antibody against PD-1, an immunoadhesin, a fusion protein, and an oligopeptide that inhibits the binding of PD-1 to PD-L1 and/or PD-L2. In some aspects, the anti-PD-1 antibody may comprises a heavy chain variable region having at least 85%, at least 90%, at least 91%, at least 92%, at least 93%, at least 94%, at least 95%, at least 96%, at least 97%, at least 98%, at least 99%, or 100% sequence identity to the sequence set forth in SEQ ID NO:22. SEQ ID NO:22 is set forth below:

QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFELY

SRLTVDKSRWQEGNVFSCSVMHEALHNHYTQKSLSLSLGK

In some aspects, the anti-PD-1 antibody comprises a light chain variable region having at least 85%, at least 90%, at least 91%, at least 92%, at least 93%, at least 94%, at least 95%, at least 96%, at least 97%, at least 98%, at least 99%, or 100% sequence identity to the sequence set forth in SEQ ID NO:19. In some embodiments, the anti-PD-1 antibody is selected from the group consisting of MDX-1106, Merck 3745, and CT-011.

The PD-L1 binding antagonist may be selected from the group consisting of an anti-PD-L1 antibody, an antigen binding fragment of the antibody against PD-L1, an immunoadhesin, a fusion protein, and an oligopeptide that inhibits the binding of PD-L1 to PD-1 and/or B7-1. In some aspects, the anti-PD-L1 antibody comprises a heavy chain variable region having at least one sequence with at least 85%, at least 90%, at least 91%, at least 92%, at least 93%, at least 94%, at least 95%, at least 96%, at least 97%, at least 98%, at least 99%, or 100% sequence identity to at least one sequence selected from the group consisting of GFTFS-$X_1$-SWIH (SEQ ID NO:1), AWI-$X_2$-PYGGS-$X_3$-YYADSVKG (SEQ ID NO:2), and RHWPGGFDY (SEQ ID NO:3), wherein $X_1$ is D or G, $X_2$ is S or L, and $X_3$ is T or S. In some embodiments, $X_1$ is D, $X_2$ is S, and $X_3$ is T. In some embodiments, the heavy chain variable region of the anti-PD-L1 antibody further comprises at least one sequence having at least 85%, at least 90%, at least 91%, at least 92%, at least 93%, at least 94%, at least 95%, at least 96%, at least 97%, at least 98%, at least 99%, or 100% sequence identity to a sequence selected from the group consisting of EVQLVESGGGLVQPGGSLRLSCAAS (SEQ ID NO:4), WVRQAPGKGLEWV (SEQ ID NO:5), RFTISADTSKNTAYLQMNSLRAEDTAVYYCAR (SEQ ID NO:6), WGQGTLVTVSA (SEQ ID NO:7), and WGQGTLVTVSS (SEQ ID NO:17).

In some embodiments, the PD-1 axis binding antagonist is selected from the group consisting of a PD-1 binding antagonist, a PD-L1 binding antagonist, and a PD-L2 binding antagonist.

The PD-1 binding antagonist may be selected from the group consisting of an anti-PD-1 antibody, an antigen binding fragment of the antibody against PD-1, an immunoadhesin, a fusion protein, and an oligopeptide that inhibits the binding of PD-1 to PD-L1 and/or PD-L2. In some aspects, the anti-PD-1 antibody may comprises a heavy chain variable region having at least 85%, at least 90%, at least 91%, at least 92%, at least 93%, at least 94%, at least 95%, at least 96%, at least 97%, at least 98%, at least 99%, or 100% sequence identity to the sequence set forth in SEQ ID NO:22. In some aspects, the anti-PD-1 antibody comprises a light chain variable region having at least 85%, at least 90%, at least 91%, at least 92%, at least 93%, at least 94%, at least 95%, at least 96%, at least 97%, at least 98%, at least 99%, or 100% sequence identity to the sequence set forth in SEQ ID NO:19. In some embodiments, the anti-PD-1 antibody is selected from the group consisting of MDX-1106, Merck 3745, and CT-011.

The PD-L1 binding antagonist may be selected from the group consisting of an anti-PD-L1 antibody, an antigen binding fragment of the antibody against PD-L1, an immunoadhesin, a fusion protein, and an oligopeptide that inhibits the binding of PD-L1 to PD-1 and/or B7-1. In some aspects, the anti-PD-L1 antibody comprises a heavy chain variable region having at least one sequence with at least 85%, at least 90%, at least 91%, at least 92%, at least 93%, at least 94%, at least 95%, at least 96%, at least 97%, at least 98%, at least 99%, or 100% sequence identity to at least one sequence selected from the group consisting of GFTFS-$X_1$-SWIH (SEQ ID NO:1), AWI-$X_2$-PYGGS-$X_3$-YYADSVKG (SEQ ID NO:2), and RHWPGGFDY (SEQ ID NO:3), wherein $X_1$ is D or G, $X_2$ is S or L, and $X_3$ is T or S. In some embodiments, $X_1$ is D, $X_2$ is S, and $X_3$ is T. In some embodiments, the heavy chain variable region of the anti-PD-L1 antibody further comprises at least one sequence having at least 85%, at least 90%, at least 91%, at least 92%, at least 93%, at least 94%, at least 95%, at least 96%, at least 97%, at least 98%, at least 99%, or 100% sequence identity to a sequence selected from the group consisting of EVQLVESGGGLVQPGGSLRLSCAAS (SEQ ID NO:4), WVRQAPGKGLEWV (SEQ ID NO:5), RFTISADTSKNTAYLQMNSLRAEDTAVYYCAR (SEQ ID NO:6), WGQGTLVTVSA (SEQ ID NO:7), and WGQGTLVTVSS (SEQ ID NO:17).

The anti-PD-L1 antibody may comprises a heavy chain variable region having at least 85%, at least 90%, at least 91%, at least 92%, at least 93%, at least 94%, at least 95%, at least 96%, at least 97%, at least 98%, at least 99%, or 100% sequence identity to a sequence set forth in the group consisting of SEQ ID NO:21, SEQ ID NO:22, SEQ ID NO:23, and SEQ ID NO:24. In some aspects, the anti-PD-L1 antibody comprises a light chain variable region having at least one sequence with at least 85%, at least 90%, at least 91%, at least 92%, at least 93%, at least 94%, at least 95%, at least 96%, at least 97%, at least 98%, at least 99%, or 100% sequence identity to a sequence selected from the group consisting of RASQ-$X_4$-$X_5$-$X_6$-T-$X_7$-$X_8$-A (SEQ ID NO:8), SAS-$X_9$-L-$X_{10}$-S(SEQ ID NO:9), and QQ-$X_{11}$-$X_{12}$-$X_{13}$-$X_{14}$-P-$X_{15}$-T (SEQ ID NO:10), wherein $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F, or W; $X_{13}$ is Y, N, A, T, G, F, or I; $X_{14}$ is H, V, P, T, or I; and $X_{15}$ is A, W, R, P, or T. In some embodiments, $X_4$ is D, $X_5$ is V, $X_6$ is S, $X_7$ is A, $X_8$ is V, $X_9$ is F, $X_{10}$ is Y, $X_{11}$ is Y, $X_{12}$ is L, $X_{13}$ is Y, $X_{14}$ is H, and $X_{15}$ is A. In some aspects, the light chain variable region of the anti-PD-L1 antibody further comprises at least one sequence with at least 85%, at least 90%, at least 91%, at least 92%, at least 93%, at least 94%, at least 95%, at least 96%, at least 97%, at least 98%, at least 99%, or 100% sequence identity to a sequence selected from the group consisting of DIQMTQSPSSL-SASVGDRVTITC (SEQ ID NO:11), WYQQKPGKAPKLLIY (SEQ ID NO:12), GVPSRFSGSGSGTDFTLTISSLQPEDFATYYC (SEQ ID NO:13), and FGQGTKVEIKR (SEQ ID NO:14). In some aspects, the anti-PD-L1 antibody comprises a light chain variable region having at least 85%, at least 90%, at least 91%, at least 92%, at least 93%, at least 94%, at least 95%, at least 96%, at least 97%, at least 98%, at least 99%, or 100% sequence identity to a sequence set forth in the group consisting of SEQ ID NO:18, SEQ ID NO:19, and SEQ ID NO:20. In some embodiments, the anti-PD-L1 antibody is selected from the group consisting of MDX-1105, YW243.55.S70, and MPDL3280A.

The PD-L2 binding antagonist may be selected from the group consisting of an antibody against PD-L2, an antigen binding fragment of the antibody against PD-L2, an immunoadhesin, a fusion protein, and an oligopeptide that inhibits the binding of PD-L2 to PD-1. In some embodiments, the PD-L2 binding antagonist is AMP-224.

Provided are also methods of treating a proliferative disease, such as cancer. The method includes the steps of administering to a subject in need of such treatment, a therapeutically effective amount of a PD-1 axis binding antagonist and a therapeutically effective amount of the benzamide compound or a pharmaceutically acceptable salt or solvate thereof.

In some embodiments, the therapeutically effective amount of the benzamide compound and the therapeutically effective amount of the PD-1 axis binding antagonist are amounts sufficient to delay the progression of cancer in the subject. In some embodiments, the therapeutically effective amounts are amounts sufficient to inhibit cancer metastasis. The specific type of cancers treatable according to the methods of the invention may be selected from the group consisting of colorectal cancer, melanoma, non-small cell lung cancer, ovarian cancer, breast cancer, pancreatic cancer, hematological malignancy, and renal cell carcinoma.

The therapeutically effective amounts may also be amounts sufficient to increase the immune function of the subject. Relative to prior to the administration of benzamide compound and the PD-1 axis binding antagonist, the therapeutically effective amounts are amounts sufficient to increase priming, activation, proliferation and/or cytolytic activity of CD8 T cells of the subject in some embodiments. In some aspects, the CD8 T cells are antigen-specific CD8 T cells. The therapeutically effective may also be amounts sufficient to increase a population of CD8 T cells in the subject, wherein the population of CD8 T cells is γIFN+, relative to prior to the administration of benzamide compound and the PD-1 axis binding antagonist. In some embodiments, the therapeutically effective amounts are amounts sufficient to increase the expression of MHC class I antigen relative to prior to the administration of benzamide compound and the PD-1 axis binding antagonist. The therapeutically effective amounts may also be amounts sufficient to increase maturation and activation of antigen presenting cells relative to prior to the administration of benzamide compound and the PD-1 axis binding antagonist. In some aspects, the increase maturation and activation of antigen presenting cells comprises increased population of CD8+ dendritic cells. Specifically, the increase maturation and activation of antigen presenting cells may comprise increased expression of CD80 and CD86 on dendritic cells.

The PD-1 axis binding antagonist may be administered intravenously, intramuscularly, subcutaneously, topically, orally, transdermally, intraperitoneally, intraorbitally, by implantation, by inhalation, intrathecally, intraventricularly, or intranasally. The benzamide compound may be administered continuously or intermittently. In some implementations, the benzamide compound is administered before the administration of the PD-1 axis binding antagonist. In other implementations, the benzamide compound is administered after the administration of the PD-1 axis binding antagonist. In some embodiments, the benzamide compound is co-administered with the PD-1 axis binding antagonist.

Provided are compositions, including pharmaceutical compositions, and methods for treating cancers using a composition comprising a benzamide compound, or a pharmaceutically acceptable salt or solvate thereof, and a CTLA4 antagonist. The benzamide compound has a formula of

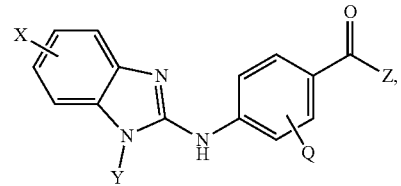

wherein: X is selected from the group consisting of H, halo, —OH, —CN, —NR'R", —OR', —SR', —OC(O)R', —NHC(O)R', —NHC(O)NR'R", —C(O)R', —NS(O)₂R', —S(O)₂NR'R", —S(O)₂R', guanidino, nitro, nitroso, —C₁-C₆ alkyl, aryl, —C₃-C₇ cycloalkyl, and 3 to 10-membered heterocycle, wherein the —C₁-C₆ alkyl, aryl, —C₃-C₇ cycloalkyl, or 3 to 10-membered heterocycle any of which may be unsubstituted or substituted with one or more of the following: halo, —OH, —CN, —NR'R", —OR', —SR', —OC(O)R', —NR'R", —NHC(O)R', —NHC(O)NR'R", —C(O)R', —NS(O)₂R', —S(O)₂NR'R", —S(O)₂R', guanidino, nitro, nitroso, —C₁-C₆ alkyl, aryl, —C₃-C₇ cycloalkyl; Y is selected from the group consisting of H, —C₁-C₆ alkyl, —C₃ cycloalkyl, aryl, 3 to 10-membered heterocycle wherein the —C₁-C₆ alkyl, —C₃-C₁₂ cycloalkyl, aryl, 3 to 10-membered heterocycle any of which may be unsubstituted or substituted with one or more of the following: -halo, —C₁-C₆ alkyl, —C₃-C₁₂ cycloalkyl, 3 to 10-membered heterocycle, aryl, OH, —CN, —OR', —SR', —OC(O), —NR'R", —NHC(O)R', —NHC(O)NR'R", —C(O)R', —NS(O)₂R', —S(O)₂NR'R", —S(O)₂R', guanidino, nitro, nitroso; R' or R" may be —H or —C₁-C₆ alkyl; Z is NHOH; and Q is selected from the group consisting of H, F, Cl, Br and I. In some embodiments, Y is selected from the group consisting of cyclopentyl, cyclohexyl, and cycloheptyl. In other embodiments, Y is selected from the group consisting of cyclopentylmethyl, cyclohexylmethyl or cycloheptylmethyl.

The CTLA4 antagonist may be selected from the group consisting of CTLA4 inhibitors that agonize the co-stimulatory pathway, CD28 inhibitors that disrupts the ability of CD8 to bind to its cognate ligand, B7 inhibitors that disrupt the ability of B7 to bind to CD28 and/or CTLA4, CD80 inhibitors that disrupt the ability of CD80 to bind to CD28 and/or CTLA4, CD86 inhibitors that disrupt the ability of CD80 to bind to CD28 and/or CTLA4. In some embodiments, the CTLA4 antagonist is selected from the group consisting of a small molecule inhibitor of CD28, CD80, CD86, and CTLA4. The CTLA4 antagonist may also be selected from the group consisting of an antisense molecule directed against CD28, CD80, CD86, and CTLA4. In other embodiments, the CTLA4 antagonist is selected from the group consisting of an adnectin directed against CD28, CD80, CD86, and CTLA4. The CTLA4 antagonist may also be selected from the group consisting of single-stranded and double-stranded RNA interference inhibitor of CD28, CD80, CD86, and CTLA4. In some embodiments, the CTLA4 antagonist is selected from the group consisting of an antibody directed to CD28, CD80, CD86, and CTLA4. In some aspects, the antibody directed to CTLA4 is selected from the group consisting of ipilimumab and tremelimumab.

The composition may further comprise a peptide antigen, for example gp100. The composition may also further comprise an anti-proliferative cytotoxic agent selected from the group consisting of an alkylating agent, an antimetabolite, vinca alkaloids, antitumor antibiotics, enzymes, lymphokines, epipodophyllotoxins, navelbene, CPT-11, anastrazole, letrazole, capecitabine, reloxafine, cyclophosphamide, ifosamide, and droloxafine.

In some aspects, the alkylating agent is selected from the group consisting of nitrogen mustards, ethylenimine derivatives, alkyl sulfonates, nitrosoureas, and triazenes. The alkylating agent may also be selected from the group consisting of Uracil mustard, Chlormethine, Cyclophosphamide, Ifosfamide, Meiphalan, Chlorambucil, Pipobroman, Triethylene-melamine, Triethylenethiophosphoramine, Busulfan, Carmustine, Lomustine, Streptozocin, Dacarbazine, and Temozolomide.

The antimetabolite is selected from the group consisting of folic acid antagonists, pyrimidine analogs, purine analogs and adenosine deaminase inhibitors. In some aspects, the antimetabolite is selected from the group consisting of Methotrexate, 5-Fluorouracil, Floxuridine, Cytarabine, 6-Mercaptopurine, 6-Thioguanine, Fludarabine phosphate, Pentostatine, and Gemcitabine.

The methods of treating cancer comprise administering to a subject in need of such treatment a therapeutically effective amount of a benzamide compound and administering to a subject in need of such treatment a therapeutically effective amount of a CTLA4 antagonist. In some embodiments, the methods of treating cancer treats solid tumors and/or refractory tumors.

In some implementations, the benzamide compound is administered before the administration of the CTLA4 antagonist. In other implementations, the benzamide compound is co-administered with the CTLA4 antagonist. In some aspects, the benzamide compound is administered intravenously In some implementations, the CTLA4 antagonist is administered intravenously. In some embodiments, the therapeutically effective amount of the CTLA4 antagonist is 0.3 to 10 mg/kg. In some aspects, the CTLA4 antagonist is administered every three weeks. In some embodiments, the CTLA4 antagonist is administered in an escalating dose.

Some methods of the invention further comprise administering an anti-proliferative cytotoxic agent. In some embodiments, the methods further comprise administering radiation therapy to the subject.

Provided are compositions, including pharmaceutical compositions comprising a benzamide compound, or a pharmaceutically acceptable salt or solvate thereof, and a DNA demethylating agent. The benzamide compound has a formula of

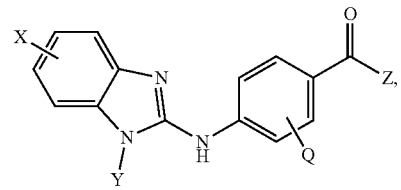

wherein: X is selected from the group consisting of H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)2NR'R", —S(O)2R', guanidino, nitro, nitroso, —C$_1$-C$_6$ alkyl, aryl, —C$_3$-C$_7$ cycloalkyl, and 3 to 10-membered heterocycle, wherein the —C$_1$-C$_6$ alkyl, aryl, —C$_3$-C$_7$ cycloalkyl, or 3 to 10-membered heterocycle, any of which may be unsubstituted or substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C$_1$-C$_6$ alkyl, aryl, —C$_3$-C$_7$ cycloalkyl; Y is selected from the group consisting of H, —C$_1$-C$_6$ alkyl, —C$_3$-C$_{12}$ cycloalkyl, aryl, 3 to 10-membered heterocycle wherein the —C$_1$-C$_6$ alkyl, —C$_3$-C$_{12}$ cycloalkyl, aryl, or 3 to 10-membered heterocycle, any of which may be unsubstituted or substituted with one or more of the following: -halo, —C$_1$-C$_6$ alkyl, —C$_3$-C$_{12}$ cycloalkyl, 3 to 10-membered heterocycle, aryl, OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso; R' or R" may be —H or —C$_1$-C$_6$ alkyl; Z is selected from the group consisting of —NHOH; and Q is selected from the group consisting of H and halo. In some embodiments, the benzamide compound is selected from the group consisting of 4-(1-(cyclohexylmethyl)-1H-benzo[d]imidazol-2-ylamino)-N-hydroxybenzamide, 4-(1-cyclohexyl-1H-benzo[d]imidazol-2-ylamino)-N-hydroxybenzamide, and 4-(1-cycloheptyl-1H-benzo[d]imidazol-2-ylamino)-N-hydroxybenzamide.

Provided are also methods of treating a proliferative disease, such as cancer. The method includes the steps of administering to a subject in need of such treatment, a therapeutically effective amount of a DNA demethylating agent and a therapeutically effective amount of the benzamide compound or a pharmaceutically acceptable salt or solvate thereof.

In certain embodiments, the DNA demethylating agent is a DNA methyltransferase inhibitor, such as a cytidine analog. In some embodiments, the cytidine analog is selected from the group consisting of: azacitidine and decitabine.

The therapeutically effective amount of the benzamide compound and the DNA demethylating agent are an amount sufficient to reduce the occurrence of hyperplasia, metaplasia, or dysplasia in cells of the patient. In a preferred embodiment the benzamide compound and the DNA demethylating agent are an amount sufficient to inhibit neoplastic, malignant, or metastatic progression of cells of the patient.

In particular implementations, the therapeutically effective amount of cytidine analog is about 15, 25, 50, 75, or 100 mg/m$^2$ per day. The cytidine analog may be administered daily for 3 to 14 days followed by 21 to 25 days rest. Alternatively, the cytidine analogy may be administered in cycles, wherein a cycle of cytidine analog administration is 28 days beginning with 3 to 14 days of cytidine analog administration followed by rest.

The cytidine analog and benzamide compound may be administered systemically. For example, the cytidine analog may be administered intravenously, subcutaneously or orally. In a particular implementation, the cytidine analog is administered subcutaneously and the benzamide compound is administered orally. In yet other implementation, the cytidine analog is administered orally and the benzamide compound is administered intravenously. In still another implementation, the cytidine analog is administered intravenously and the benzamide compound is administered orally. In one implementation, both the cytidine analog and the benzamide compound are administered orally.

DETAILED DESCRIPTION

Figure 1:
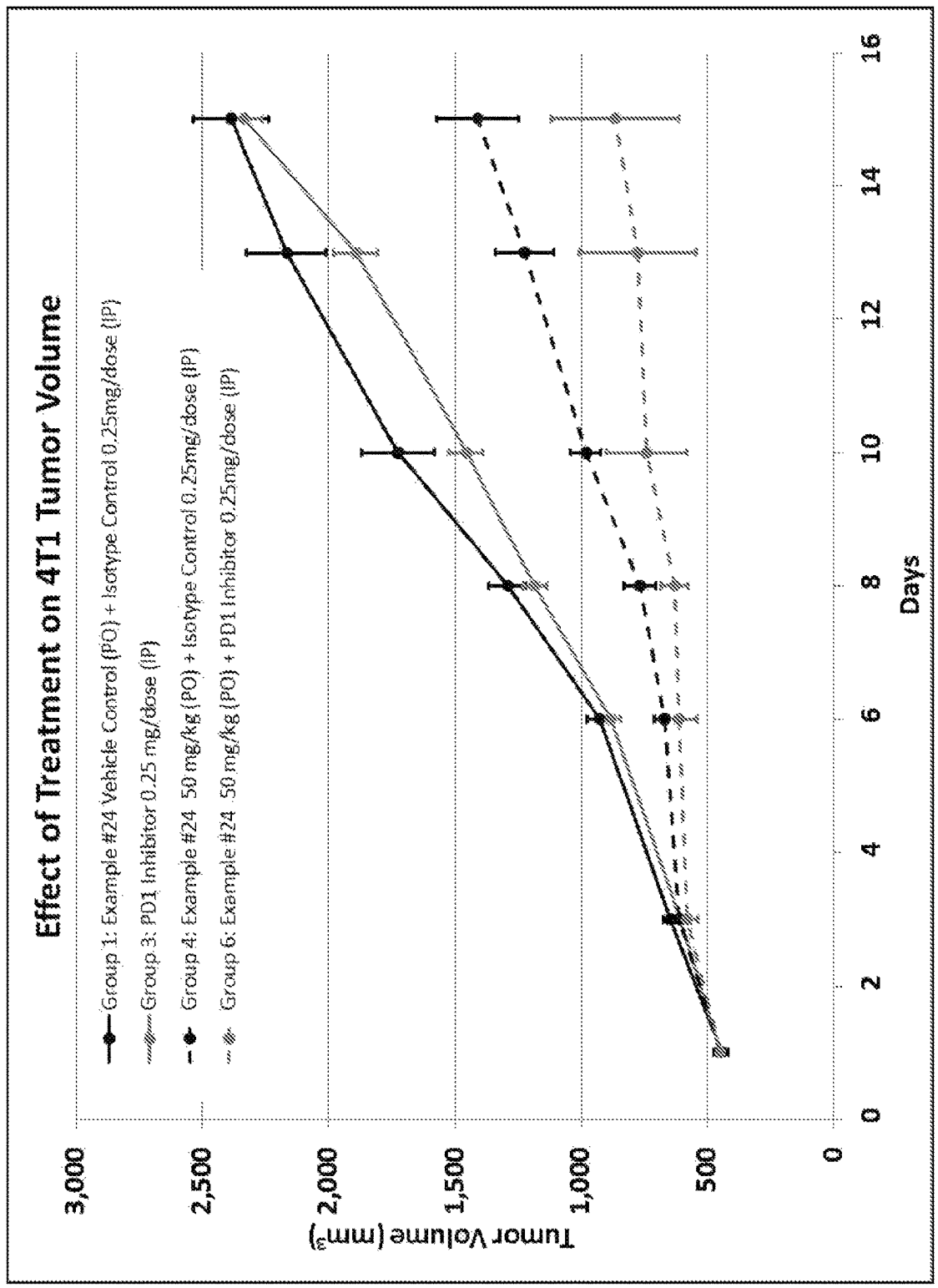
FIG. 1 depicts the effect of Compound ID #24 alone, a PD-1 axis binding antagonist alone, and a combination of the two therapeutic agents on 4T1 murine breast tumor volume growth.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, the term "treating" refers to an alleviation, in whole or in part, of symptoms associated with a disorder or disease (e.g., cancer or a tumor syndrome), or slowing, or halting of further progression or worsening of those symptoms. Treatment is contemplated in living entities including but not limited to mammals (particularly humans) as well as other mammals of economic or social importance, including those of an endangered status. Further examples include livestock or other animals generally bred for human consumption and domesticated companion animals. Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

As used herein, the term "preventing" refers to the prevention of the onset, recurrence or spread, in whole or in part, of the disease or disorder (e.g., cancer), or a symptom thereof.

As used herein, the term "tumor" refers to all neoplastic cell growth and proliferation, whether malignant or benign, and all pre-cancerous and cancerous cells and tissues. As used herein, the term "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

As used herein, the term "cancer" includes, but is not limited to, solid tumors and blood born tumors. Thus the term "cancer" includes that of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

As used herein, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, the term "cancer cells" refer to any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

As used herein, the term "relapsed" refers to a situation where a subject, that has had a remission of cancer after a therapy, has a return of cancer cells.

As used herein, the term "refractory" or "resistant" refers to a circumstance where a subject, even after intensive treatment, has residual cancer cells in the body.

As used herein, the term "chemoresistant cancer" refers a type of cancer when cancer that has been responding to chemotherapy suddenly begins to grow because cancer cells are not responsive to the effects of chemotherapy.

As used herein, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

As used herein, the term "effective amount" in connection with the benzamide compound and the PD-1 axis binding antagonist, the CTLA4 antagonist, and/or the DNA demethylating agent refers to an amount capable of alleviating, in whole or in part, symptoms associated with a disorder, or slowing or halting further progression or worsening of those symptoms, or preventing or providing prophylaxis for the disorder, in a subject at risk for the disorder. The effective amount of the benzamide compound and the PD-1 axis binding antagonist, the CTLA4 antagonist, and/or the DNA demethylating agent, for example in a pharmaceutical composition, may be at a level that will exercise the desired effect. For example, in the case of cancer, the effective amount is an amount capable of alleviating, in whole or in part, symptoms associated with a cancer, for example cancer, or slowing or halting further progression or worsening of those symptoms, or preventing or providing prophylaxis for the cancer, in a subject at risk for cancer. As will be apparent to those skilled in the art, it is to be expected that the effective amount of the benzamide compound and of the PD-1 axis binding antagonist, the CTLA4 antagonist, and/or the DNA demethylating agent herein may vary depending on the severity of the indication being treated.

As used herein, the term "pharmaceutically acceptable" refers to molecular entities and compositions that are physiologically tolerable and do not typically produce an allergic or similar untoward reaction, such as gastric upset, dizziness and the like, when administered to a subject.

Thus the term "pharmaceutically acceptable carrier" refers to a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier must be "acceptable" in the sense of being compatible with the other ingredients of the formulation and not injurious to a subject to whom it is administered. Nor should an acceptable carrier alter the specific activity of the subject compounds.

As used herein, the term "pharmaceutically acceptable salt" encompasses non-toxic acid and base addition salts of the compound to which the term refers. Acceptable non-toxic acid addition salts include those derived from organic and inorganic acids or bases. Examples of such salts include but are not limited to the following: salts of hydro bromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulphuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the benzamide compound or the PD-1 axis binding antagonist, the CTLA4 antagonist, and/or the DNA demethylating agent with a suitable acid in a manner known by those skilled in the art.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein, the term "prodrug" refers a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —NO$_2$, —ONO, or —ONO$_2$ moieties. Prodrugs can typically be prepared using well-known methods, such as those described in *Burger's Medicinal Chemistry and Drug Discovery* (Manfred E. Wolff ed., 5th ed. 1995) and *Design of Prodrugs* (H. Bundgaard ed., Elsevier, N.Y. 1985).

As used herein, the term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

As used herein, the term "unit-dosage form" refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. A unit-dosage form may be administered in fractions or multiples thereof. Examples of a unit-dosage form include an ampoule, syringe, and individually packaged tablet and capsule.

As used herein, the term "multiple-dosage form" is a plurality of identical unit-dosage forms packaged in a single container to be administered in segregated unit-dosage form. Examples of a multiple-dosage form include a vial, bottle of tablets or capsules, or bottle of pints or gallons.

As used herein, and unless otherwise specified, the terms "composition," "formulation," and "dosage form" are intended to encompass products comprising the specified ingredient(s) (in the specified amounts, if indicated), as well as any product(s) which result, directly or indirectly, from combination of the specified ingredient(s) in the specified amount(s).

As used herein, the term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

As used herein, the term "dysfunctional" also includes refractory or unresponsive to antigen recognition, specifically, impaired capacity to translate antigen recognition into downstream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function," as used herein, refers to inducing, causing, or stimulating a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies and a Disclosed benzamide compound.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration of at least the same as the treatment duration, at least 1.5.times, 2.0 times, 2.5.times, or 3.0 times length of the treatment duration.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, $F(ab')_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the alpha and gamma chains and four $C_H$ domains for 1.1 and E isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated alpha, delta, epsilon, gamma and pt respectively. The gamma and alpha classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "$V_H$" and "$V_L$," respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_{H1}$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_{H1}$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody that retains or has modified FcR binding capability. Examples of antibody fragments include linear antibody, single-chain antibody molecules and multispecific antibodies formed from antibody fragments.

"Diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain, which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available compleX crystal structures.

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, $5^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "$V_H$ subgroup III consensus framework" comprises the consensus sequence obtained from the amino acid sequences in variable heavy subgroup III of Kabat et al., supra. In one embodiment, the $V_H$ subgroup III consensus framework amino acid sequence comprises at least a portion or all of each of the following sequences: EVQLVESGG-GLVQPGGSLRLSCAAS (HC-FR1, SEQ ID NO:4), WVRQAPGKGLEWV (HC-FR2, SEQ ID NO:5), RFTI-SADTSKNTAYLQMNSLRAEDTAVYYCAR (HC-FR3, SEQ ID NO:6), WGQGTLVTVSA (HC-FR4, SEQ ID NO:7).

A "$V_L$ kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSL-SASVGDRVTITC (LC-FR1, SEQ ID NO: 11), WYQQKPGKAPKLLIY (LC-FR2, SEQ ID NO: 12), GVPSRFSGSGSGTDFTLTISSLQPEDFATYYC (LC-FR3, SEQ ID NO:13), FGQGTKVEIKR (LC-FR4, SEQ ID NO:14).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

As used herein, the term "immunoadhesin" designates antibody-like molecules that combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2 or the extracellular or PD-L1 or PD-L2 binding portions of PD-1, fused to a constant domain of an immunoglobulin sequence, such as a PD-L1 ECD Fc, a PD-L2 ECD Fc, and a PD-1 ECD-Fc, respectively.

Immunoadhesin combinations of Ig Fc and extracellular domain of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

A "PD-1 oligopeptide," "PD-L1 oligopeptide," or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well-known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. USA.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J Immunol. Meth.*, 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581 (1991); Kang, A. S. et al. *Proc. Natl. Acad. Sci. USA*, 88:8363 (1991), and Smith, G. P., *Current Opin. Biotechnol.*, 2:668 (1991).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG 1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a γ receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daeron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The term "synergy" or "synergistic effect" may be defined as an effect that is more than additive (Chou, 2006, *Pharmacolog Reviews*, 58: 621-681). Synergistic interactions amongst drug combinations are highly desirable and sought after since they can result in increased efficacy, decreased dosage, reduced side toxicity, and minimized development of resistance when used clinically (Chou, 2006). The two most popular methods for evaluating drug interactions in combination therapies are isobologram and combination index (CI) (Zhao et al., 2004, *Clinical Cancer Res* 10:7994-8004). There are numerous studies in the cancer therapy field where drug combinations are evaluated to counter the development of drug resistance and to minimize drug doses, use the CI index to evaluate synergy. CI is based on the approach of Chou and Talalay 1984 (*Adv. Enzyme Regul.* 22:27-55) and relies on the median effect principle and the multiple-drug effect equation. CI can readily be calculated using the program CompuSyn (CompuSyn, Paramus, N.J.). An interaction is slightly synergistic if the CI value is 0.85-0.9, moderately synergistic if the CI value is 0.7-0.85, synergistic if the CI value is 0.3-0.7, strongly synergistic if the CI value is 0.1-0.3, and very strongly synergistic if the CI value is <0.1 (Table 1) (Chou 2006). However, in cancer therapy literature, the values of CI that define synergism may vary. For example in Lin et al., 2007, *Carcinogenesis* 28: 2521-2529, synergism between drugs was defined as CI<1 while in Fischel et al., 2006, *Preclinical Report* 17: 807-813, synergism was defined as CI<0.8. However, these references agree that synergism can be defined as CI<0.8.

TABLE 1

Description of synergism or antagonism in drug combination studies analyzed with the combination index method

| Range of Combination Index | Description |
|---|---|
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.9-1.1 | Nearly additive |
| 1.1-1.2 | Slight antagonism |
| 1.2-1.45 | Moderate antagonism |
| 1.45-3.3 | Antagonism |
| 3.3-10 | Strong antagonism |
| >10 | Very strong antagonism |

The present invention relates to the discovery that the combination of a PD-1 axis binding antagonist, a CTLA4 antagonist, and/or a DNA demethylating agent with a benzamide compound produces synergistic therapeutic effects.

One avenue of treating a proliferative disease, such as cancer, is cancer immunotherapy. This therapeutic strategy aims to improve the immune system's recognition of unhealthy cells in a subject. Accordingly, induction of a strong cytotoxic T cell response is necessary. Optimal T cell activation requires two signals (Lafferty 1975): 1) the interaction between the T cell receptor and specific antigen (Bretscher 1970) and 2) engagement of co-stimulatory receptors on the surface of the T cell with co-stimulatory ligands expressed by the antigen-presenting cell (APC). This model further provides for the discrimination of self from non-self and immune tolerance (Bretscher 1970, Bretscher 1999, Jenkins 1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. (Lenschow 1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki 2007, Thompson 2006). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Ahmadzadeh 2009). This may be due to exploitation of PD-L1 signaling mediated by PD-L1 expressing tumor cells interacting with PD-1 expressing T cells to result in attenuation of T cell activation and evasion of immune surveillance (Sharpe 2002, Keir 2008). Therefore, inhibition of the PD-L1/PD-1 interaction may enhance CD8+ T cell-mediated killing of tumors.

The inhibition of PD-1 axis signaling through its direct ligands (e.g., PD-L1, PD-L2) has been proposed as a means to enhance T cell immunity for the treatment of cancer (e.g., tumor immunity). Moreover, similar enhancements to T cell immunity have been observed by inhibiting the binding of PD-L1 to the binding partner B7-1. Furthermore, combining inhibition of PD-1 signaling with other signaling pathways that are deregulated in tumor cells may further enhance treatment efficacy. However, an optimal therapeutic treatment would combine blockade of PD-1 receptor/ligand interaction with an agent that directly inhibited tumor growth, optionally further including unique immune enhancing properties not provided by PD-1 blockade alone.

Because CTLA4 appears to undermine T cell activation, attempts have been made to block CTLA4 activity in murine models of cancer immunotherapy. In mice implanted with immunogenic tumors, administration of anti-CTLA4 antibody enhanced tumor rejection (Leach 1996) although little effect was seen with poorly immunogenic tumors such as SMI mammary carcinoma or B16 melanoma. Enhanced antitumor immunity was seen when anti-CTLA4 antibody was given with granulocyte-macrophage colony-stimulating factor (GM-CSF)-transduced B16 cell vaccine and was associated with depigmentation, suggesting that at least part of the antitumor response was antigen-specific against "self" melanocyte differentiation antigens (van Elsas 1999, van Elsas 2001). In a transgenic murine model of primary prostate cancer, administrating anti-CTLA4 antibody plus GM-CSF-expressing prostate cancer cells reduced the incidence and histological severity of prostate cancer and led to prostatitis in normal mice, again suggesting an antigen-specific immune response against self-antigens in tumor rejection (Hurwitz 2000). Furthermore, because many human tumor antigens are normal self-antigens, breaking tolerance against self may be critical to the success of cancer immunotherapy. The favorable tumor responses from CTLA4 blockade in conjunction with tumor vaccines in murine models led to interest in using CTLA4 blockade in human cancer immunotherapy.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

The present invention relates to the discovery that the combination of a PD-1 axis binding antagonist, a CTLA4 antagonist, and/or a DNA demethylating agent with a benzamide compound produces synergistic therapeutic effects in the treatment of proliferative diseases, including cancer. The combination also produces synergistic therapeutic effects in slowing the progression of proliferative diseases. The invention provides for combination compositions, including pharmaceutical composition, comprising a PD-1 axis binding antagonist, a CTLA4 antagonist, and/or a DNA demethylating agent and a benzamide compound. The combination demonstrates superior cytotoxic/anti-tumor activity, for example anti-metastatic activity. Accordingly, the compositions and pharmaceutical compositions may be used to treat proliferative diseases including cancer. In some embodiments, the administration of the compositions and pharmaceutical compositions of the invention enhances immunogenicity, such as increasing tumor immunogenicity for the treatment of cancer. In one aspect, administering the compositions and pharmaceutical compositions to a subject enhances the immune function of the subject.

Thus, in a preferred embodiment, the therapeutic methods of the invention comprise the administration of a therapeutically effective amount of benzamide compound or analogs thereof in combination with a therapeutically effective amount of one or more PD-1 axis binding antagonists, CTLA4 antagonists, and/or DNA demethylating agents. In some implementations, the methods involve the administration of a therapeutic amount of a pharmaceutical composition that includes the benzamide compound and/or a pharmaceutically acceptable salt thereof and the PD-1 axis binding antagonist, CTLA4 antagonist, and/or DNA demethylating agent to a subject in need thereof, preferably a subject in which a proliferative disease has been diagnosed.

In some embodiments, subject is diagnosed with a cancer having elevated levels of T cell infiltration. The subject may also have enhanced priming, activation, proliferation and/or cytolytic activity of the CD8 T cells in the individual relative to prior to the administration of the PD-1 axis binding antagonist and the benzamide compound. The CD8 T cell priming may be characterized by elevated CD44 expression and/or enhanced cytolytic activity in CD8 T cells. In some embodiments, the CD8 T cell activation is characterized by an elevated frequency of γIFN$^+$ CD8 T cells. In some embodiments, the CD8 T cell is an antigen-specific T-cell. In some embodiments, the immune evasion by signaling through PD-L1 surface expression is inhibited.

In some embodiments, the cancer cells in the subject may have elevated expression of MHC class I antigen expression relative to prior to the administration of the PD-1 axis binding antagonist, CTLA4 antagonist, and/or DNA demethylating agent and the disclosed benzamide compound.

In some embodiments, the antigen presenting cells in the individual have enhanced maturation and activation relative prior to the administration of the PD-1 axis binding antagonist, CTLA4 antagonist, and/or DNA demethylating agent and the benzamide compound. In some embodiments, wherein the antigen presenting cells are dendritic cells. In some embodiments, the maturation of the antigen presenting cells is characterized by increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the individual are reduced relative prior to the administration of the PD-1 axis binding antagonist, such as an anti-PD-L1 antibody, and the benzamide compound.

A therapeutic amount is an amount sufficient to treat a proliferative disease, which further includes the prevention of progression of a proliferative disease to a neoplastic, malignant or metastatic state, e.g. reducing the occurrences of hyperplasia, metaplasia, or dysplasia or inhibits neoplastic, malignant, or metastatic progression of cells in a subject. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell 1976, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 Dalton cell surface protein, etc. (see Robbins and Angell, 1976, pp. 84-90 for characteristics associated with a transformed or malignant phenotype). Further examples include leukoplakia, a benign-appearing hyperplastic or dysplastic lesion of the epithelium, and Bowen's disease, a carcinoma in situ, which are pre-neoplastic lesions indicative of the desirability of prophylactic intervention. In another example, fibrocystic disease including cystic hyperplasia, mammary dysplasia, adenosis, or benign epithelial hyperplasia is indicates desirability of prophylactic intervention.

Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Non-limiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macrophages and $CD8^+$ T cells) or endothelial cells that may differentiate into blood vessel structures in the process of angiogenesis or vasculogenesis.

In another aspect of the invention, the subject or disease entity exhibiting one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t(14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

Determination of an effective amount of the disclosed composition is within the capability of those skilled in the art, especially in light of the detailed disclosure provided herein. The effective amount of a pharmaceutical composition used to effect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of benzamide compound or the PD-1 axis binding antagonist, CTLA4 antagonist, and/or DNA demethylating agent for addition to a cancer cell also includes the determination of an effective therapeutic amount, including the formulation of an effective dose range for use in vivo, including in humans.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the benzamide compound or the PD-1 axis binding antagonist, CTLA4 antagonist, and/or DNA demethylating agent to result in the slowing of expansion of the cancer cells would preferably result in a concentration at or near the target tissue that is effective in slowing cellular expansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

The addition of a therapeutically effective amount of composition encompasses any method of dosing of a compound. Dosing of the benzamide compound or the PD-1 axis binding antagonist, CTLA4 antagonist, and/or DNA demethylating agent may include single or multiple administrations of any of a number of pharmaceutical compositions that include the disclosed composition as active ingredients. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed composition may be administered prior to, concurrently with (e.g. coadministration), or after administration of a second pharmaceutical composition that may or may not include the compound. The benzamide compound and PD-1 axis binding antagonist, CTLA4 antagonist, and/or DNA demethylating agent of the composition may also be administered concurrently or one of the elements of the composition may be administered prior to the other. If the compositions or elements of the composition are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment. For example, in one implementation, the PD-1 axis binding antagonist, CTLA4 antagonist, and/or DNA demethylating agent is administered in a 28-day cycle beginning with 3-14 days of daily treatment with the PD-1 axis binding antagonist, CTLA4 antagonist, and/or DNA demethylating agent following by rest for the rest of the cycle. In another implementation, the PD-1 axis binding antagonist, CTLA4 antagonist, and/or DNA demethylating agent is administered daily for 3-14 days followed by 21-25 days of rest.

The invention further encompasses kits that facilitate the administration of the benzamide compound and the a PD-1 axis binding antagonist, CTLA4 antagonist, and/or DNA demethylating agent to a diseased entity. An example of such a kit includes one or more unit dosages of the benzamide compound and of the PD-1 axis binding antagonist, CTLA4 antagonist, and/or DNA demethylating agent. The unit dosage would be enclosed in a preferably sterile container and would be comprised of the benzamide compound or the PD-1 axis binding antagonist, CTLA4 antagonist, and/or DNA demethylating agent and a pharmaceutically acceptable carrier. In another aspect, the unit dosage would comprise one or more lyophilates of the benzamide compound and the PD-1 axis binding antagonist, CTLA4 antagonist, and/or DNA demethylating agent. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

The compositions of the invention may take any physical form necessary depending on a number of factors including the desired method of administration and the physicochemical and stereochemical form taken by the benzamide compound and the PD-1 axis binding antagonist, CTLA4 antagonist, and/or DNA demethylating agent or pharmaceutically acceptable salts thereof. Such physical forms include a solid, liquid, gas, sol, gel, aerosol, or any other physical form now known or yet to be disclosed. In some aspects, the compositions comprise a pharmaceutically acceptable salt of a PD-1 axis binding antagonist, CTLA4 antagonist, and/or DNA demethylating agent and of a benzamide compound. The compositions may be with or without any pharmaceutically acceptable additive.

In some aspects, the compositions may further comprise a pharmaceutically acceptable carrier. Carriers include any substance that may be administered with the benzamide compound and the PD-1 axis binding antagonist, CTLA4 antagonist, and/or DNA demethylating agent with the intended purpose of facilitating, assisting, or helping the administration or other delivery of the compound. Carriers include any liquid, solid, semisolid, gel, aerosol or anything else that may be combined with the benzamide compound and the PD-1 axis binding antagonist, CTLA4 antagonist, and/or DNA demethylating agent to aid in their administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The compositions of the invention may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in *Remington's Pharmaceutical Sciences* by E. W. Martin, hereby incorporated by reference in its entirety. In some embodiments, the compositions of the invention may include additional effective compounds of a distinct chemical formula or biological structure from the benzamide compound and the PD-1 axis binding antagonist, CTLA4 antagonist, and/or DNA demethylating agent. In some aspects, the additional effective compound may have the same or a similar molecular target as the target or it may act upstream or downstream of the molecular target of the benzamide compound and the PD-1 axis binding antagonist, CTLA4 antagonist, and/or DNA demethylating agent with regard to one or more biochemical pathways.

Examples of the additional effective compound include nucleic acid binding compositions, antiemetic compositions, hematopoietic colony stimulating factors, anxiolytic agents, and analgesic agents.

Examples of nucleic acid binding compositions include, but are not limited to, cis-diamminedichloro platinum (II) (cisplatin), doxorubicin, 5-fluorouracil, taxol, and topoisomerase inhibitors such as etoposide, teniposide, irinotecan and topotecan. Examples of antiemetic compositions include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron. Examples of hematopoietic colony stimulating factors include, but are not limited to, filgrastim, sargramostim, molgramostim and epoietin alfa. Alternatively, the pharmaceutical composition including the benzamide compound and the DNA demethylating agent may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Analgesic agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

The additional effective compound may be a chemotherapeutic agent, which is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); Δ-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Nicolaou et al., Angew. Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL8), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an antiestrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

The additional effective compound may be an anti-proliferative compound, such as an anti-proliferative cytotoxic agent. Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®), Ifosfamide, Meiphalan, Chlorambucil, Pipobroman, Triethylenemelamine, Triethylenethiophosphoramine, Busulfan, Carmustine, Lomustine, Streptozocin, Dacarbazine, and Temozolomide;

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine;

Natural products and their derivatives (for example, *vinca* alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as TAXOL®, Mithramycin, Deoxyco-formycin, Mitomycin-C, L-Asparaginase, Interferons (especially IFN-a), Etoposide, and Teniposide;

Navelbene;

CPT-11;

Anastrazole;

Letrazole;

Capecitabine;

Reloxafine;

Cyclophosphamide;

Ifosamide; and

Droloxafine.

The anti-proliferative compound may also be a microtubule-affecting agent. A microtubule-affecting agent interferes with cellular mitosis and is well known in the art for their anti-proliferative cytotoxic activity. Microtubule-affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione, [1 S-[1R*,3R*(E),7R*, 10S*,11R*, 12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Ser. No. 09/506,481 filed on Feb. 17, 2000), and derivatives thereof, and other microtubule-disrupter agents. Additional anti-proliferative compounds include, discodermolide, estramustine, nocodazole, MAP4, and the like. Examples of such agents are also described in the scientific and patent literature, see, e.g., Bulinski 1997, Panda 1997, Muhlradt 1997, Nicolaou 1997, Vasquez 1997, and Panda 1996.

Also suitable candidates for the anti-proliferative compound are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particularly preferred class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors. Other anti-angiogenic agents include matrix metalloproteinase inhibitors. Also suitable for use in the combination chemotherapeutic methods of the invention are other VEGF inhibitors, such as anti-VEGF antibodies and small molecules such as ZD6474 and SU6668. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors.

The additional effective compound may also be selected from the group consisting of co-stimulatory pathway agonist other than the CTLA4 antagonist (e.g. an immunostimulant), a tubulin stabilizing agent (e.g., pacitaxol, epothilone, taxane, etc.), IXEMPRA™, Dacarbazine, Paraplatin, Docetaxel, one or more peptide vaccines, MDX-1379 Melanoma Peptide Vaccine, one or more gp100 peptide vaccine, fowlpox-PSA-TRICOM™ vaccine, vaccinia-PSA-TRICOM™ vaccine, MART-1 antigen, sargramostim, ticilimumab, Combination Androgen Ablative Therapy. Examples of co-stimulatory pathway modulators include, but are not limited to, the following: agatolimod, blinatumomab, CD40 ligand, AG4263, eritoran, anti-OX40 antibody, ISF-154, and SGN-70.

A non-limiting example of a peptide antigen would be a gp100 peptide comprising, or alternatively consisting of, the sequence selected from the group consisting of: IMDQVPFSV (SEQ ID NO:15), and YLEPGPVTV (SEQ ID NO:16). Such a peptide may be administered orally, or preferably by injection subcutaneously at 1 mg emulsified in incomplete Freund's adjuvant (IFA) injected subcutaneously in one extremity, and 1 mg of either the same or a different peptide emulsified in IFA may be injected in another extremity.

The combination comprising a PD-1 axis binding antagonist, CTLA4 antagonist, and/or DNA demethylating agent with a benzamide derivative may also include the addition of an anti-proliferative cytotoxic agent either alone or in combination with radiation therapy, also known as radiotherapy. The term "radiation therapy" includes, but is not limited to, x-rays or gamma rays that are delivered from either an externally applied source such as a beam or by implantation of small radioactive sources.

In cases where it is desirable to render aberrantly proliferative cells quiescent in conjunction with or prior to treatment with the chemotherapeutic methods of the invention, hormones and steroids (including synthetic analogs) can also be administered to the patient. Thus the additional effective compound may also be hormones, steroids, or synthetic analogs thereof selected from the group consisting of 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Also suitable for use as an antiproliferative cytostatic agent is CASODEX® which renders androgen-dependent carcinomas non-proliferative. Yet another example of a cytostatic agent is the antiestrogen Tamoxifen, which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

Pharmaceutical compositions include materials capable of modifying the physical form of a dosage unit. In one non-limiting example, the composition includes a material that forms a coating that holds in the compound. Materials that may be used in such a coating, include, for example, sugar, shellac, gelatin, or any other inert coating agent.

Pharmaceutical compositions may also be prepared as a gas or aerosol. Aerosols encompass a variety of systems including colloids and pressurized packages. Delivery of a composition in this form may include propulsion of a pharmaceutical composition through use of liquefied gas or other compressed gas or by a suitable pump system. Aerosols may be delivered in single-phase, bi-phasic, or tri-phasic systems.

In specific aspects of the invention, the pharmaceutical composition is in the form of a solvate. Such solvates are produced by the dissolution of the benzamide compound and the PD-1 axis binding antagonist, CTLA4 antagonist, and/or DNA demethylating agent in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the benzamide compound and the PD-1 axis binding antagonist, CTLA4 antagonist, and/or DNA demethylating agent to treat the affliction without serious complications arising from the use of the solvent in a majority of patients.

Pharmaceutical compositions including the benzamide compound and the PD-1 axis binding antagonist, CTLA4 antagonist, and/or DNA demethylating agent may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

The invention also provides methods of treating a proliferative disease, including cancer, comprising administering to a subject a therapeutically effective amount of a PD-1 axis binding antagonist, CTLA4 antagonist, and/or DNA demethylating agent and administering to a subject a therapeutically effective amount of a benzamide compound. In a preferred embodiment of this invention, a method is provided for the synergistic treatment of cancerous tumors. Advantageously, the synergistic method of this invention reduces the development of tumors, reduces tumor burden, or produces tumor regression in a mammalian host.

Cancers that may be treated by pharmaceutical compositions include, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; other tumors including melanoma, xenoderma pigmentosum, keratoactanthoma, seminoma, thyroid follicular cancer, and teratocarcinoma; melanoma, unresectable stage m or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof. Most preferably, the invention is used to treat accelerated or metastatic cancers of the bladder, pancreatic cancer, prostate cancer, melanoma, non-small cell lung cancer, colorectal cancer, and breast cancer.

Other examples of types of cancer that the pharmaceutical compositions of the invention can be used to treat include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), Chronic myelomonocytic leukemia (CMML), chronic lymphocytic leukemia ("CLL"), hairy cell leukemia, myelodysplastic syndromes, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The therapeutically effective amount of the benzamide compound and the PD-1 axis binding antagonist, CTLA4 antagonist, and/or DNA demethylating agent may be a synergistically effective amount. The synergistically effective of the benzamide compound is less than the amount needed to treat proliferative diseases if the benzamide compound was administered without a PD-1 axis binding antagonist, CTLA4 antagonist, and/or DNA demethylating agent. Similarly, the synergistically effective amount of a PD-1 axis binding antagonist, CTLA4 antagonist, and/or DNA demethylating agent is less than the amount needed to treat cancer or if the PD-1 axis binding antagonist, CTLA4 antagonist, and/or DNA demethylating agent was administered without the benzamide compound.

The synergistically effective amounts of the benzamide compound and of the PD-1 axis binding antagonist, CTLA4 antagonist, and/or DNA demethylating agent may be defined by the synergism factor as represented by a CI value. There is synergism between compounds when the CI is less than about 0.8, alternatively less than about 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1.

Methods of administering the PD-1 axis binding antagonist, CTLA4 antagonist, and/or DNA demethylating agent and the benzamide compound include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material. A pharmaceutical composition formulated so as to be administered by injection may be prepared by dissolving the benzamide compound and the PD-1 axis binding antagonist, CTLA4 antagonist, and/or DNA demethylating agent with water so as to form a solution. In addition, a surfactant may be added to facilitate the formation of a homogeneous solution or suspension. Surfactants include any complex capable of non-covalent interaction with the benzamide compound and the PD-1 axis binding antagonist, CTLA4 antagonist, and/or DNA demethylating agent so as to facilitate dissolution or homogeneous suspension of the compound.

Administration of the PD-1 axis binding antagonist, CTLA4 antagonist, and/or DNA demethylating agent and the benzamide compound may be systemic or local. Local administration is administration of the benzamide compound or the PD-1 axis binding antagonist, CTLA4 antagonist, and/or DNA demethylating agent to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The benzamide compound and the PD-1 axis binding antagonist, CTLA4 antagonist, and/or DNA demethylating agent may be delivered in the context of a vesicle such as a liposome or any other natural or synthetic vesicle.

In some implementations of the methods of treating a proliferative disease, the methods may comprise administering an additional treatment modality. Such treatment modalities include but are not limited to, radiotherapy (radiation therapy), surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. Combination therapies may act synergistically. That is, the combination of the therapies is more effective than either therapy administered alone. This results in a situation in which lower dosages of both treatment modalities may be used effectively. This in turn reduces the toxicity and side effects, if any, associated with the administration either modality without a reduction in efficacy.

In a preferred embodiment, the composition of the invention is administered in combination with a therapeutically effective amount of radiotherapy. In some aspects, the additional therapy is gamma irradiation. The radiotherapy may be administered concurrently with, prior to, or following the administration of the pharmaceutical composition including the benzamide compound and PD-1 axis binding antagonist, CTLA4 antagonist, and/or DNA demethylating agent. The radiotherapy may act additively or synergistically with the pharmaceutical composition including the compound and a PD-1 axis binding antagonist, CTLA4 antagonist, and/or DNA demethylating agent. This particular aspect of the invention would be most effective in cancers known to be responsive to radiotherapy. Cancers known to be responsive to radiotherapy include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, other CNS neoplasms, or any other such tumor now known or yet to be disclosed.

In other embodiments, the composition of the invention is administered in combination with the additional therapy is surgery. In some aspects, the additional therapy is a combination of radiation therapy and surgery. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described hereabove.

In some implementations of the methods of treating a proliferative, the compositions of the invention may be used in combination with treatment of cancer ex vivo. One example of such a treatment is an autologous stem cell transplant. In this method, a subject or diseased entity's autologous hematopoietic stem cells are harvested and purged of all cancer cells. A therapeutic amount of a pharmaceutical composition including the benzamide compound and the PD-1 axis binding antagonist, CTLA4 antagonist, and/or DNA demethylating agent may then be administered to the subject or diseased entity prior to restoring the entity's bone marrow by addition of either the patient's own or donor stem cells.

The PD-1 Axis Binding Antagonist

A PD-1 axis binding antagonist is a molecule that inhibits the interaction of a PD-1 axis binding partner with either one or more of its binding partner, so as to remove T-cell dysfunction resulting from signaling on the PD-1 signaling axis with a result being to restore or enhance T-cell function (e.g., proliferation, cytokine production, target cell killing). A PD-1 axis binding antagonist includes, but is not limited to, a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

A PD-1 binding antagonist is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition).

In some embodiments, the PD-1 binding antagonist is an anti-PD-1 antibody. For example, the PD-1 binding antagonist may be an anti-PD-1 antibody selected from the group consisting of MDX-1106 (CAS Registry Number: 946414-94-4; alternatively named MDX-1106-04, ONO-4538, BMS-936558 or Nivolumab), Merck 3745 (alternatively named MK-3475 or SCH-900475), and CT-01 (alternatively named hBAT or hBAT-1).

In some embodiments, the PD-1 binding antagonist is an immunoadhesin, for example an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. AMP-224, also known as B7-DCIg, is a PD-L2-Fc fusion soluble receptor.

In some embodiment, the PD-1 an isolated anti-PD-1 antibody comprising a heavy chain variable region comprising the heavy chain variable region amino acid sequence from SEQ ID NO:22 and/or a light chain variable region comprising the light chain variable region amino acid sequence of:

```
                                           (SEQ ID NO: 19)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In a still further embodiment, provided is an isolated anti-PD-1 antibody comprising a heavy chain and/or a light chain sequence, wherein the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence SEQ ID NO:22; the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence SEQ ID NO:19.

A PD-L1 binding antagonist is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition).

In some embodiments, a PD-L1 binding antagonist is an anti-PD-L1 antibody. In some embodiments, the anti-PD-L1 antibody is a humanized antibody. In some embodiments, the anti-PD-L1 antibody is a human antibody. In some embodiments, the anti-PD-L1 antibody is an antibody fragment selected from the group consisting of Fab, Fab'-SH, Fv, scFv, and (Fab')$_2$ fragments.

In some aspects, the heavy chain of the anti-PD-L1 antibody may a comprise heavy chain variable region having at least one sequence with at least 85%, at least 90%, at least 91%, at least 92%, at least 93%, at least 94%, at least 95%, at least 96%, at least 97%, at least 98%, at least 99%, or 100% sequence identity to at least one sequence selected from the group consisting of GFTFS-$X_1$-SWIH (SEQ ID NO:1), AWI-$X_2$-PYGGS-$X_3$-YYADSVKG (SEQ ID NO:2), and RHWPGGFDY (SEQ ID NO:3), wherein $X_1$ is D or G, $X_2$ is S or L, and $X_3$ is T or S. In preferred embodiments, $X_1$ is D, $X_2$ is S, and $X_3$ is T.

Alternatively, the heavy chain of the anti-PD-L1 antibody may comprise a heavy chain variable region having at least one sequence having at least 85%, at least 90%, at least 91%, at least 92%, at least 93%, at least 94%, at least 95%, at least 96%, at least 97%, at least 98%, at least 99%, or 100% sequence identity to a sequence selected from the group consisting of EVQLVESGGGLVQPGGSLRLSCAAS (SEQ ID NO:4), WVRQAPGKGLEWV (SEQ ID NO:5), RFTI-SADTSKNTAYLQMNSLRAEDTAVYYCAR (SEQ ID NO:6), WGQGTLVTVSA (SEQ ID NO:7), and WGQGTLVTVSS (SEQ ID NO:17).

In some embodiments, the anti-PD-L1 antibody comprises a heavy chain variable region having at least 85%, at least 90%, at least 91%, at least 92%, at least 93%, at least 94%, at least 95%, at least 96%, at least 97%, at least 98%, at least 99%, or 100% sequence identity to a sequence set forth in the group consisting of SEQ ID NO:21, SEQ ID NO:22, SEQ ID NO:23, and SEQ ID NO:24. SEQ ID NO:23 is set forth below:

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS

SEQ ID NO:24 is set forth below:

EVQLVESGGGLVQPGGSLRLSCAASGFTESDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLEPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

In some aspects, the light chain of the anti-PD-L1 antibody may a comprise a light chain variable region having at least one sequence with at least 85%, at least 90%, at least 91%, at least 92%, at least 93%, at least 94%, at least 95%, at least 96%, at least 97%, at least 98%, at least 99%, or 100% sequence identity to a sequence selected from the group consisting of RASQ-$X_4$-$X_5$-$X_6$-T-$X_7$-$X_8$-A (SEQ ID NO:8), SAS-$X_9$-L-$X_{10}$-S(SEQ ID NO:9), and QQ-$X_{11}$-$X_{12}$-$X_{13}$-$X_{14}$-P-$X_{15}$-T (SEQ ID NO: 10), wherein $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F, or W; $X_{13}$ is Y, N, A, T, G, F, or I; $X_{14}$ is H, V, P, T, or I; and $X_{15}$ is A, W, R, P, or T. In preferred embodiment, $X_4$ is D, $X_5$ is V, $X_6$ is S, $X_7$ is A, $X_8$ is V, $X_9$ is F, $X_{10}$ is Y, $X_{11}$ is Y, $X_{12}$ is L, $X_{13}$ is Y, $X_{14}$ is H, and $X_{15}$ is A.

Alternatively, the light chain of the anti-PD-L1 antibody may comprise a light chain variable region having at least one sequence having at least 85%, at least 90%, at least 91%, at least 92%, at least 93%, at least 94%, at least 95%, at least 96%, at least 97%, at least 98%, at least 99%, or 100% sequence identity to a sequence selected from the group consisting of DIQMTQSPSSLSASVGDRVTITC (SEQ ID NO:11), WYQQKPGKAPKLLIY (SEQ ID NO:12), GVPSRFSGSGSGTDFTLTISSLQPEDFATYYC (SEQ ID NO:13), and FGQGTKVEIKR (SEQ ID NO:14). In a preferred embodiment, the anti-PD-L1 antibody comprises a light chain variable region having at least 85%, at least 90%, at least 91%, at least 92%, at least 93%, at least 94%, at least 95%, at least 96%, at least 97%, at least 98%, at least 99%, or 100% sequence identity to a sequence set forth in the group consisting of SEQ ID NO:18, SEQ ID NO:19, and SEQ ID NO:20.

SEQ ID NO:20 is set forth below:

DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments, the anti-PD-L1 antibody comprises a heavy chain variable region comprising the amino acid sequence of:

(SEQ ID NO: 21)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA and/or a light chain variable region comprising the amino acid sequence of:

(SEQ ID NO: 18)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

The anti-PD-L1 binding antagonist may also be selected from the group consisting of YW243.55.S70 (heavy and light chain variable region sequences shown in SEQ ID Nos. 20 and 21, respectively), MPDL3280A and MDX-1105 (also known as BMS-936559).

A PD-L2 binding antagonist is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

In some aspects, the antibody described herein (such as an anti-PD-1 antibody, an anti-PD-L1 antibody, or an anti-PD-L2 antibody) may comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for a composition comprising an anti-PD-L1, an anti-PD-1, or an anti-PD-L2 antibody or antigen binding fragment thereof as provided herein and at least one pharmaceutically acceptable carrier. In some embodiments, the anti-PD-L1, anti-PD-1, or anti-PD-L2 antibody or antigen binding fragment thereof administered to the individual is a composition comprising one or more pharmaceutically acceptable carrier. Any of the pharmaceutically acceptable carrier described herein or known in the art may be used.

The CTLA4 Antagonist

Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, belatacept, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP1212422B1. Additional CTLA4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA4 antibodies that can be used in a method of the present invention include, for example, those disclosed in: WO 98/42752; U.S. Pat. Nos. 5,977,318, 6,207,156, 6,682,736. 7,109,003, and 7,132,281; Hurwitz 1998; Camacho 2004 (antibody CP-675206); and Mokyr 1998. In some preferred embodiments, the anti-CTLA4 antibody is selected from the group consisting of ipilimumab and tremelimumab.

Additional CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway, antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway. In some implementations, the CTLA4 antagonist may be an anti-B7-1 antibody, an anti-B7-2 antibody, an anti-B7-H4 antibody.

The anti-CTLA4 antibody may preferably be administered at about 0.3-10 mg/kg, or the maximum tolerated dose. In an embodiment, of the invention, a dosage of CTLA-4 antibody is administered about every three weeks. Alternatively, the CTLA-4 antibody may be administered by an escalating dosage regimen including administering a first dosage of CTLA-4 antibody at about 3 mg/kg, a second dosage of CTLA-4 antibody at about 5 mg/kg, and a third dosage of CTLA-4 antibody at about 9 mg/kg. In another specific embodiment, the escalating dosage regimen includes administering a first dosage of CTLA-4 antibody at about 5 mg/kg and a second dosage of CTLA-4 antibody at about 9 mg/kg.

The present invention also provides an escalating dosage regimen, which includes administering an increasing dosage of CTLA-4 antibody about every six weeks. In one aspect of the present invention, a stepwise escalating dosage regimen is provided, which includes administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg. In another aspect of the present invention, a stepwise escalating dosage regimen is provided, which includes administering a first dosage of 5 mg/kg, a second dosage of 5 mg/kg, and a third dosage of 9 mg/kg.

The actual dosage employed may be varied depending upon the requirements of the patient and the severity of the condition being treated. Determination of the proper dosage for a particular situation is within the skill of the art. Generally, treatment is initiated with smaller dosages that are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

The DNA Demethylating Agent

An example of a DNA demethylating agent that made used in the composition includes a DNA methyltransferase inhibitor, which inhibits the transfer of a methyl group to DNA. In one specific embodiment, the DNA methyltransferase inhibitor is an analogue of cytosine. These cytosine analogues are incorporated into the DNA during replication before covalently linking with DNA methyltransferases (DNMTs), thus leading to global loss of gene methylation (Christman J. K., *Oncogene* 21:5483-95, 2002).

In another embodiment, the DNA methyltransferase inhibitor may be an analogue of cytidine. In a specifc aspect, the cytidine analogues are any compound that is structurally related to cytidine or deoxycytidine and functionally mimics and/or antagonizes the action of cytidine or deoxycytidine. The cytidine analogue may be 5-azacytidine (azacitidine), 5-aza-2'-deoxycytidine (decitabine), 1-β-D-arabinofuranosylcytosine (Cytarabine or ara-C), pseudoiso-cytidine (psi ICR), 5-fluoro-2'-deoxycytidine (FCdR), 2'-deoxy-2',2'-difluorocytidine (Gemcitabine), 5-aza-2'-deoxy-2',2'-difluorocytidine, 5-aza-2'-deoxy-2'-fluorocytidine, 1-β-D-ribofuranosyl-2(1H)-pyrimidinone (Zebularine), 2',3'-dideoxy-5-fluoro-3'-thiacytidine (Emtriva), 2'cyclocytidine (Ancitabine), 1-β-D-arabinofuranosyl-5-azacytosine (Fazarabine or ara-AC), 6-azacytidine (6-aza-CR), 5,6-dihydro-5-azacytidine (dH-aza-CR), N4-pentyloxy-carbonyl-5'-deoxy-5-fluorocytidine (Capecitabine), N4-octadecyl-cytarabine, or elaidic acid cytarabine.

Azacitidine is 4-amino-1-β-D-ribofuranozyl-s-triazin-2 (1H)-one, also known as VIDAZA®. Its empirical formula is $C_8H_{12}N_4O_5$, the molecular weight is 244. Azacitidine is a white to off-white solid that is insoluble in acetone, ethanol and methyl ketone; slightly soluble in ethanol/water (50/50), propylene glycol and polyethylene glycol; sparingly soluble in water, water-saturated octanol, 5% dextrose in water, N-methyl-2-pyrrolidone, normal saline and 5% Tween 80 in water, and soluble in dimethylsulfoxide (DMSO). VIDAZA® is approved for treatment in patients with higher-risk MDS. It is supplied in a sterile form for reconstitution as a suspension for subcutaneous injection or reconstitution as a solution with further dilution for intravenous infusion. Vials of VIDAZA® contain 100 mg of azacitidine and 100 mg of mannitol as a sterile lyophilized powder.

Decitabine is 4-amino-1-(2-deoxy-β-D-erythro-pentofuranosyl)-1,3,5-triazin-2(1H)one, also known as DACOGEN®. Its empirical formula is $C_8H_{12}N_4O_4$, the molecular weight is 228.21. Decitabine is a fine, white to almost white powder that is slightly soluble in ethanol/water (50/50), methanol/water (50/50) and methanol; sparingly soluble in water, and soluble in dimethylsulfoxide (DMSO). Treatment of cancer cell models with decitabine leads to suppression of growth and apoptosis through re-expression of silenced genes (Bender et al., *Cancer Res* 58:95-101, 1998; Herman et al., *N Engl J Med* 349:2042-54, 2003) and through the activation of p53 and p21Waf1/Cip1 (Zhu et al., *J Biol Chem* 279:15161-6, 2004). Recent studies have identified that decitabine causes G2 arrest, reduces clonogenic survival, and inhibits growth in cells while causing DNA fragmentation and activating the ATM and ATR DNA repair pathways (Palii et al., *Mol Cell Biol* 28:752-71, 2008). DACOGEN® is approved for treatment in patients with myelodisplastic syndromes. It is supplied in a clear colorless glass vial as white sterile lyophilized powder for injection. Each 20 mL, as a single dose, glass vial contains 50 mg decitabine, 68 mg monobasic potassium phosphate (potassium dihydrogen phosphate) and 11.6 mg sodium hydrochloride.

As used herein, and unless otherwise specified, a compound that is a DNA demethylating agent described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

A compound that is a DNA demethylating agent described herein may encompass isotopically enriched analogs. For example, one or more hydrogen position(s) in a compound may be enriched with deuterium and/or tritium. Other suitable isotopes that may be enriched at particular positions of a compound include, but are not limited to, C-13, C-14, N-15, O-17, and/or O-18. In one embodiment, a compound described herein may be enriched at more than one position with isotopes, that are the same or different. As used herein, the terms "cytosine analogue" and "cytdine analogue" encompass the free base of the cytosine analogue or cytidine analogue, or a salt, solvate (e.g. hydrate), hydrate, cocrystal, complex, prodrug, precursor, metabolite, and/or derivative thereof. The terms "cytosine analogue" and "cytdine analogue" may also refer to the free base of the cytosine analogue or cytdine analogue, or a salt, solvate, hydrate, cocrystal or complex thereof. In certain embodiments, a cytidine analog referred to herein encompasses the free base of the cytidine analog, or a pharmaceutically acceptable salt, solvate, or hydrate thereof. In one embodiment, the free base or the pharmaceutically acceptable salt or solvate is a solid. In another embodiment, the free base or the pharmaceutically acceptable salt or solvate is a solid in an amorphous form. In yet another embodiment, the free base or the pharmaceutically acceptable salt or solvate is a solid in a crystalline form.

In some aspects, the pharmaceutically acceptable salt of the cytosine analogue or cytidine analogue may be acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenyl-propionate, phosphate, picrate, pivalate, propionate, salicylate, succinate, sulfate, tartrate, thiocyanate, tosylate, or undecanoate salts.

In one embodiment, azacitidine is formulated for injection as a sterile lyophilized powder and is supplied in a single-use vial containing 100 mg of azacitidine and 100 mg of mannitol. Azacitidine for injection is intended for intravenous injection after reconstitution as a solution with further dilution. Azacitidine for injection is intended for subcutaneous injection after reconstitution as a suspension.

In one embodiment, decitabine is formulated for injection as a white to almost white sterile lyophilized powder that is supplied in a clear colorless glass vial. Each vial (a single dose of 20 mL) contains 50 mg of decitabine, 68 mg of monobasic potassium phosphate (potassium dihydrogen phosphate) and 11.6 mg of sodium hydroxide.

The Benzamide Compound

The benzamide compound used in the compositions of the invention is preferably a compound with the formula of:

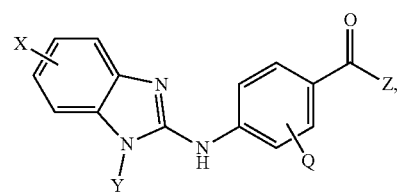

The group denoted by X may be any of H, halo, —OH, —CN, —COOR', —OR', —SR', —OC(O)R', —NHR', —NR'R", —NHC(O)R', —NHC(O)NR'R", —C(O)NR'R", —NS(O)₂R', —S(O)₂NR'R", —S(O)₂R', guanidino, nitro, nitroso, —C₁-C₆ alkyl, aryl, —C₃-C₇ cycloalkyl, and 3 to 10-membered heterocycle, wherein the —C₁-C₆ alkyl, aryl, —C₃-C₇ cycloalkyl, or 3 to 10-membered heterocycle any of which may be unsubstituted or substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C$_1$-C$_6$ alkyl, aryl, —C$_3$-C$_7$ cycloalkyl.

The group denoted by Y may be any of H, —C$_1$-C$_6$ alkyl, —C$_3$-C$_{12}$ cycloalkyl, aryl, 3 to 10-membered heterocycle wherein the —C$_1$-C$_6$ alkyl, —C$_3$-C$_{12}$ cycloalkyl, aryl, 3 to 10-membered heterocycle any of which may be unsubstituted or substituted with one or more of the following: -halo, —C$_1$-C$_6$ alkyl, —C$_3$-C$_{12}$ cycloalkyl, 3 to 10-membered heterocycle, aryl, OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso. In some aspects, the group denoted by Y may be any of cyclopentyl, cyclohexyl, cycloheptyl, cyclopentylmethyl, cyclohexylmethyl, or cycloheptylmethyl.

The group denoted by Z may be —NHOH.

The group denoted by Q may be any of H or halo. Halo groups include any halogen. Examples include but are not limited to —F, —Cl, —Br, or —I.

The group denoted by R, R', or R" may be —H or —C$_1$-C$_6$ alkyl. In some embodiments, R' and/or R" may be attached to the N or O atom. In some aspects, the R' and R" are taken together with the atoms to which they are attached to form a 3- to 8-membered or 3- to 10-membered cyclic structure.

A —C$_1$-C$_6$ alkyl group includes any straight or branched, saturated or unsaturated, substituted or unsubstituted hydrocarbon comprised of between one and six carbon atoms. Examples of —C$_1$-C$_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —C$_1$-C$_6$ alkyl groups may include any applicable chemical moieties. Examples of groups that may be substituted onto any of the above listed —C$_1$-C$_6$ alkyl groups include but are not limited to the following examples: -halo, —C$_1$-C$_6$ alkyl, —O—(C$_1$-C$_6$ alkyl), C$_3$-C$_7$ cycloalkyl, 3 to 10-membered heterocycle, aryl, —OH, —CN, —COOR', —OR', —SR', —OC(O)R', —NHR', —NR'R", —NHC(O)R', —C(O)NHR', —NS(O)$_2$R', —S(O)$_2$N(R')$_2$, or —S(O)$_2$R' groups.

An aryl group includes any unsubstituted or substituted phenyl or napthyl group. Examples of groups that may be substituted onto ay aryl group include, but are not limited to: -halo, —C$_1$-C$_6$ alkyl, —O—(C$_1$-C$_6$ alkyl), —C$_3$-C$_7$ cycloalkyl, 3 to 10-membered heterocycle, aryl, —OH, —CN, —COOR', —OR', —SR', —OC(O)R', —NHR', —NR'R", —NHC(O)R', —C(O)NHR', —C(O)NEtR', —NS(O)$_2$R', R', —S(O)$_2$N(R')$_2$, or —S(O)$_2$R' groups.

A —C$_3$-C$_7$ cycloalkyl group includes any 3-, 4-, 5-, 6-, or 7-membered substituted or unsubstituted non-aromatic carbocyclic ring while a —C$_3$-C$_{12}$ cycloalkyl group includes any 3-, 4-, 5-, 6-, 7-, 8-, 9-, 10-, 11-, or 12-membered substituted or unsubstituted non-aromatic carbocyclic ring. Examples of —C$_3$-C$_7$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1,4-cyclohexadienyl, -1,3-cycloheptadienyl, and -1,3,5-cycloheptatrienyl groups. Examples of —C$_3$-C$_{12}$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1,4-cyclohexadienyl, -1,3-cycloheptadienyl, -1,3,5-cycloheptatrienyl, cyclooctyl, cyclononyl and cyclodecyl groups. The C$_3$-C$_7$ cycloalkyl groups and C$_3$-C$_{12}$ cycloalkyl groups also include substituted or unsubstituted non-aromatic carbo-bicyclic ring. Examples of bicyclic rings include, but are not limited to, bicyclo[3.1.0]hexyl, bicyclo[2.2.0]hexyl, bicyclo[4.1.0]heptyl, bicyclo[3.2.0]heptyl and bicyclo[3.1.1]heptyl. Examples of groups that may be substituted onto —C$_3$-C$_7$ cycloalkyl groups and —C$_3$-C$_{12}$ cycloalkyl groups include, but are not limited to: -halo, —C$_1$-C$_6$ alkyl, —C$_3$-C$_7$ cycloalkyl, 3 to 10-membered heterocycle, aryl, —OH, —CN, —COOR', —OR', —SR', —OC(O)R', —NHR', —NR'R", —NHC(O)R', —NRC(O)NR'R", —C(O)NR'R", —NRS(O)$_{12}$R', —S(O)$_{12}$NR'R", or —S(O)$_{1-2}$R' groups. wherein R' and R" may be independently H, C$_1$-C$_6$ alkyl, aryl or 3 to 10 membered heterocycle, or R' and R" are taken together with the atoms to which they are attached to form a 3 to 10 membered cyclic structure.

A heterocycle may be any optionally substituted saturated, unsaturated or aromatic cyclic moiety wherein said cyclic moiety is interrupted by at least one heteroatom selected from O, S or N. Heterocycles may be monocyclic or polycyclic rings. For example, suitable substituents include halogen, halogenated C$_{1-6}$ alkyl, halogenated C$_{1-6}$ alkoxy, amino, amidino, amido, azido, cyano, guanidino, hydroxyl, nitro, nitroso, urea, —OR, —NR'R", —OS(O)$_2$R'; —OS(O)$_2$OR', —S(O)$_2$OR', —S(O)$_{0-2}$R', —C(O)OR', —C(O)NR'R", —OP(O)OR, —P(O)OR, —SO$_2$NR'R", —NRS(O)$_2$R' or —NRC(O)NR'R", wherein R' and R" may be independently H, C$_1$-C$_6$ alkyl, aryl or 3 to 10 membered heterocycle, or R' and R" are taken together with the atoms to which they are attached to form a 3 to 10 membered cyclic structure.

Possible substituents of heterocycle groups include halogen (Br, Cl, I or F), cyano, nitro, oxo, amino, C$_{1-4}$ alkyl (e.g., CH$_3$, C$_2$H$_5$, isopropyl) C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO$_4$C$_{1-4}$ alkyl, CO$_4$C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienapyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The benzamide compound and its intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include, but are not limited to keto-enol and imine-enamine isomerizations. In another example illustrated graphically below, proton migration between the 1-position, 2-amino and 3-position nitrogen atoms of a 2-aminobenzimidazole ring may occur. As a result, Formulas Ia, Ib and Ic are tautomeric forms of each other:

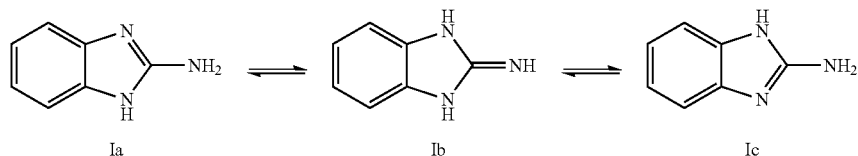 [SMILES: Nc1nc2ccccc2[nH]1 ; N=c1[nH]c2ccccc2[nH]1 ; Nc1nc2ccccc2[nH]1]

Benzamide compound further encompasses any other physiochemical or sterochemical form that the disclosed benzamide compound may assume. Such forms include diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

In some aspects, the benzamide compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the benzamide compound with a suitable acid in a manner known by those skilled in the art.

The invention further encompasses aspects in which a protecting group is added to the compound. One skilled in the art would recognize that during the synthesis of complex molecules, one group on the benzamide compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group Removal of the protecting group may be referred to as deprotection. Examples of compounds to be protected in some syntheses include hydroxy groups, amine groups, carbonyl groups, carboxyl groups and thiols.

Many protective groups and reagents capable of introducing them into synthetic processes have been and are continuing to be developed today. A protecting group may result from any chemical synthesis that selectively attaches a group that is resistant to certain reagents to the chemical group to be protected without significant effects on any other chemical groups in the molecule, remains stable throughout the synthesis, and may be removed through conditions that do not adversely react with the protected group, nor any other chemical group in the molecule. Multiple protecting groups may be added throughout a synthesis and one skilled in the art would be able to develop a strategy for specific addition and removal of the protecting groups to and from the groups to be protected.

Protecting groups, reagents that add those groups, preparations of those reagents, protection and deprotection strategies under a variety of conditions, including complex syntheses with mutually complementary protecting groups are all well known in the art. Nonlimiting examples of all of these may be found in Green et al, *Protective Groups in Organic Chemistry* 2nd Ed., (Wiley 1991), and Harrison et al, *Compendium of Synthetic Organic Methods*, Vols. 1-8 (Wiley, 1971-1996) both of which hereby incorporated by reference in its entirety.

Racemates, individual enantiomers, or diasteromers of the benzamide compound may be prepared by specific synthesis or resolution through any method now known or yet to be disclosed. For example, the benzamide compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

Non-limiting examples of benzamide compounds are:

ID# 1

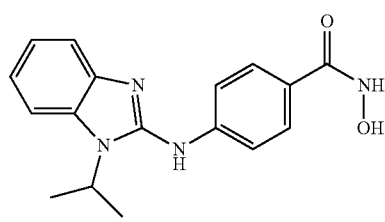

N-hydroxy-4-(1-isopropyl-1H-benzo[d]imidazol-2-ylamino)benzamide

ID# 2

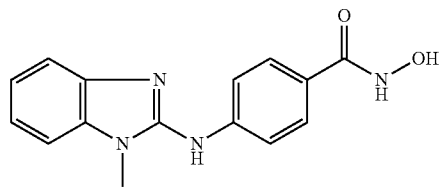

N-hydroxy-4-(1-methyl-1H-benzo[d]imidazol-2-ylamino)benzamide

ID# 3

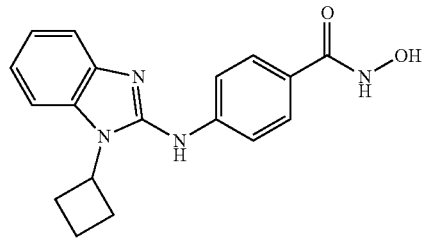

4-(1-cyclobutyl-1H-benzo[d]imidazol-2-ylamino)-N-hydroxybenzamide

ID# 4

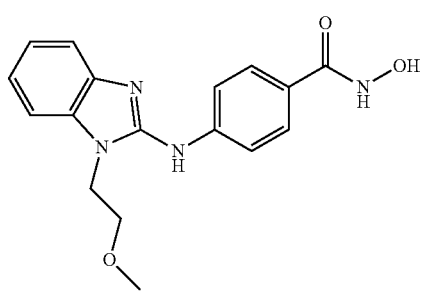

N-hydroxy-4-(1-(2-methoxyethyl)-1H-benzo[d]imidazol-2-ylamino)benzamide

ID# 5

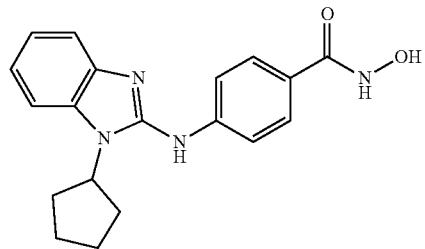

4-(1-cyclopentyl-1H-benzo[d]imidazol-2-ylamino)-N-hydroxybenzamide

ID# 6

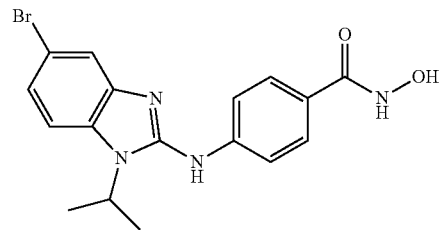

4-(5-bromo-1-isopropyl-1H-benzo[d]imidazol-2-ylamino)-N-hydroxybenzamide

ID# 7

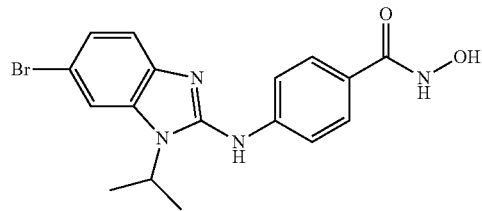

4-(6-bromo-1-isopropyl-1H-benzo[d]imidazol-2-ylamino)-N-hydroxybenzamide

ID# 8

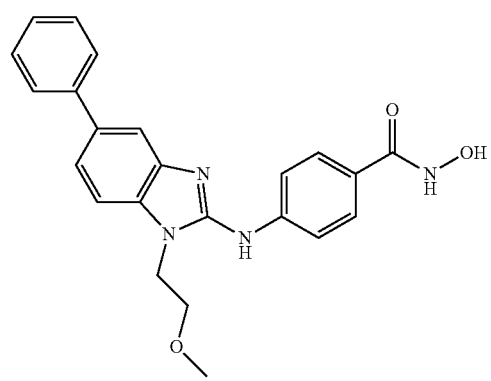

N-hydroxy-4-(1-(2-methoxyethyl)-5-phenyl-1H-benzo[d]imidazol-2-ylamino)benzamide

ID# 9

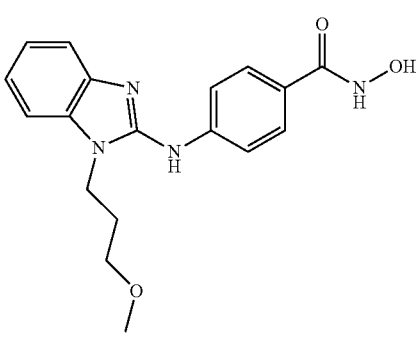

N-hydroxy-4-(1-(3-methoxypropyl)-1H-benzo[d]imidazol-2-ylamino)benzamide

ID# 10

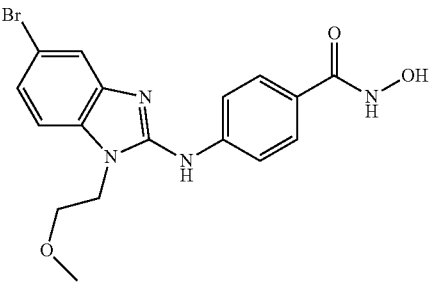

4-(5-bromo-1-(2-methoxyethyl)-1H-benzo[d]imidazol-2-ylamino)-N-hydroxybenzamide

ID# 11

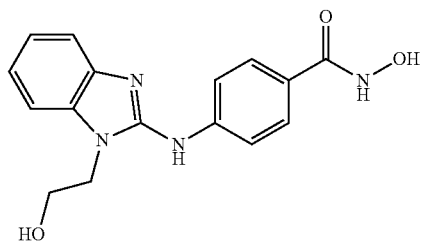

N-hydroxy-4-(1-(2-hydroxyethyl)-1H-benzo[d]imidazol-2-ylamino)benzamide

ID# 12

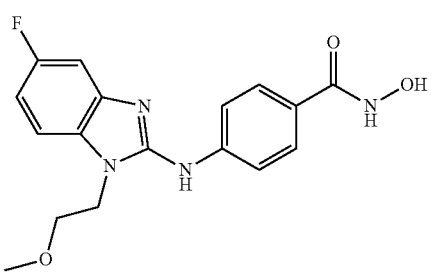

4-(5-fluoro-1-(2-methoxyethyl)-1H-benzo[d]imidazol-2-ylamino)-N-hydroxybenzamide

ID# 13

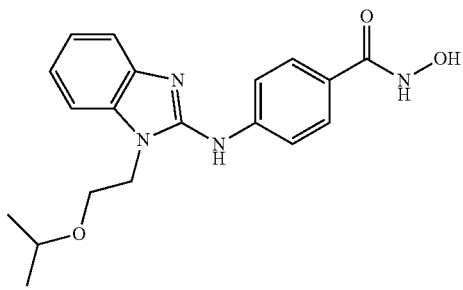

N-hydroxy-4-(1-(2-isopropoxyethyl)-1H-benzo[d]imidazol-2-ylamino)benzamide

ID# 14

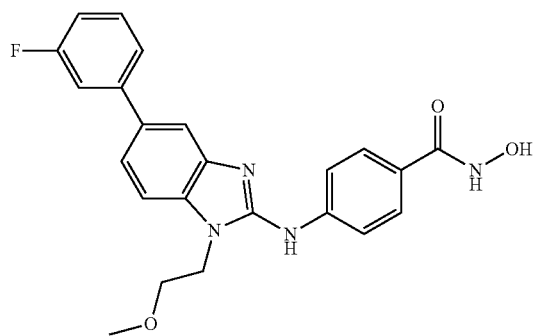

4-(5-(3-fluorophenyl)-1-(2-methoxyethyl)-1H-benzo[d]imidazol-2-ylamino)-N-hydroxybenzamide

ID# 15

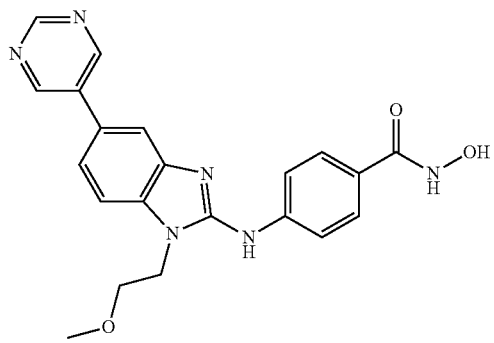

N-hydroxy-4-(1-(2-methoxyethyl)-5-(pyrimidin-5-yl)-1H-benzo[d]imidazol-2-ylamino)benzamide

ID# 16

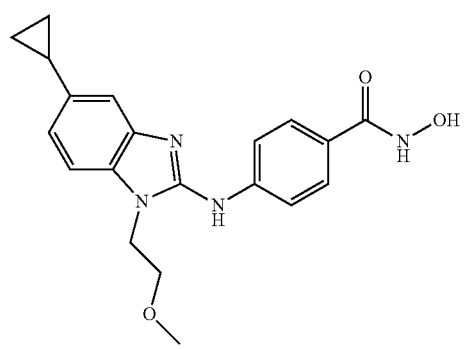

4-(5-cyclopropyl-1-(2-methoxyethyl)-1H-benzo[d]imidazol-2-ylamino)-N-hydroxybenzamide

ID# 17

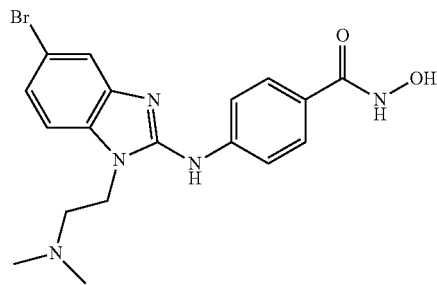

4-(5-bromo-1-(2-(dimethylamino)ethyl)-1H-benzo[d]imidazol-2-ylamino)-N-hydroxybenzamide

ID# 18

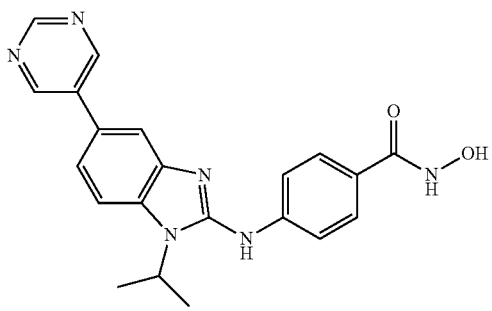

N-hydroxy-4-(1-isopropyl-5-(pyrimidin-5-yl)-1H-benzo[d]imidazol-2-ylamino)benzamide -continued

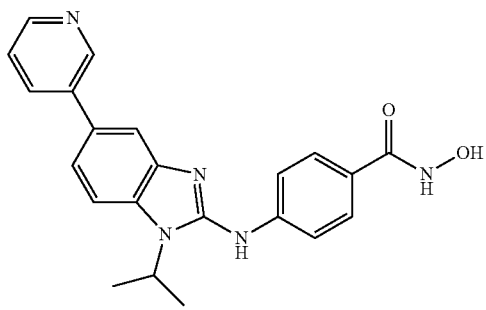

ID# 19

N-hydroxy-4-(1-isopropyl-5-(pyridin-3-yl)-1H-benzo[d]imidazol-2-ylamino)benzamide

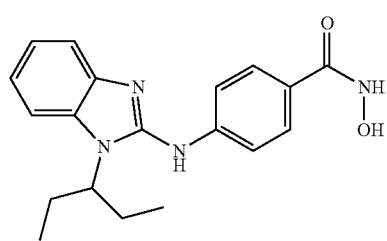

ID# 20

N-hydroxy-4-(1-(pentan-3-yl)-1H-benzo[d]imidazol-2-ylamino)benzamide

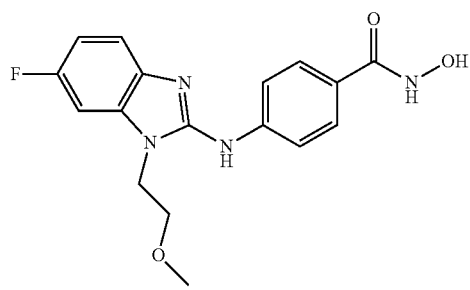

ID# 21

4-(6-fluoro-1-(2-methoxyethyl)-1H-benzo[d]imidazol-2-ylamino)-N-hydroxybenzamide

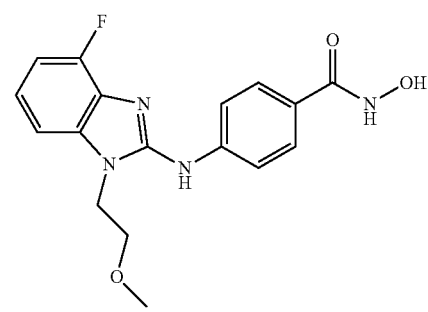

ID# 22

4-(4-fluoro-1-(2-methoxyethyl)-1H-benzo[d]imidazol-2-ylamino)-N-hydroxybenzamide -continued

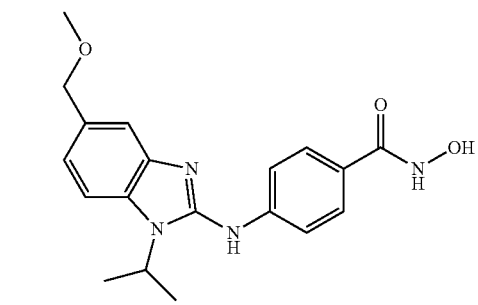

ID# 23

N-hydroxy-4-(1-isopropyl-5-(methoxymethyl)-1H-benzo[d]imidazol-2-ylamino)benzamide

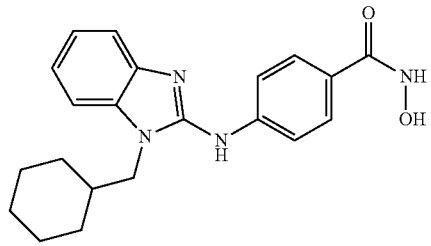

ID# 24

4-(1-(cyclohexylmethyl)-1H-benzo[d]imidazol-2-ylamino)-N-hydroxybenzamide

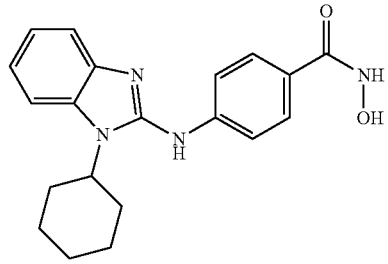

ID# 25

4-(1-(cyclohexyl-1H-benzo[d]imidazol-2-ylamino)-N-hydroxybenzamide

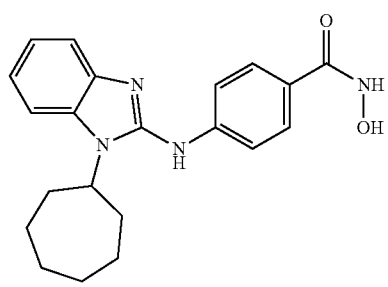

ID# 26

4-(1-cycloheptyl-1H-benzo[d]imidazol-2-ylamino)-N-hydroxybenzamide

Additional examples include:
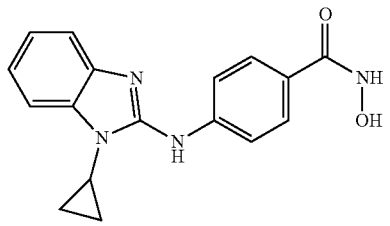
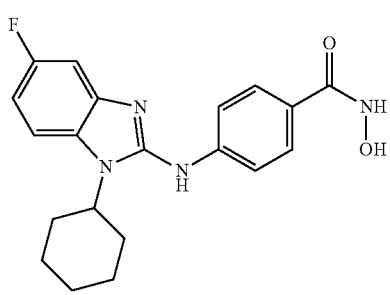
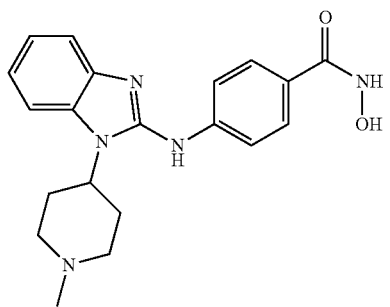
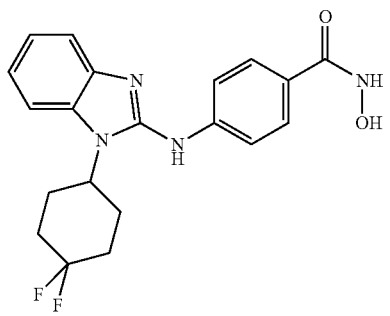
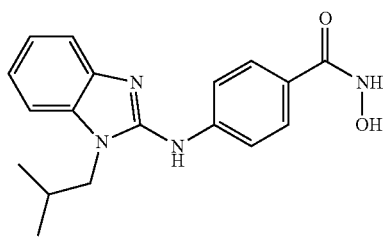
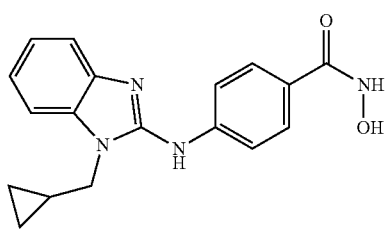
-continued
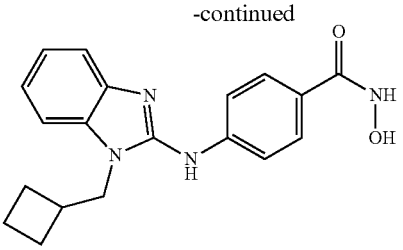
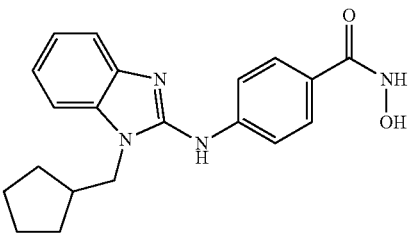
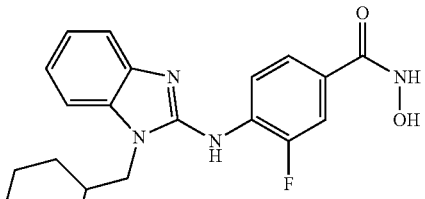
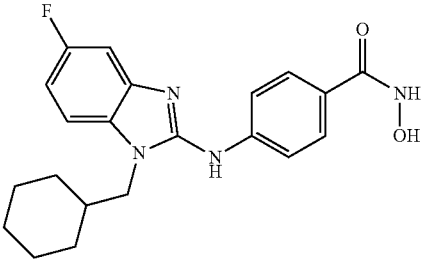
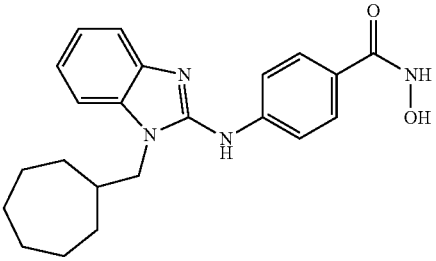
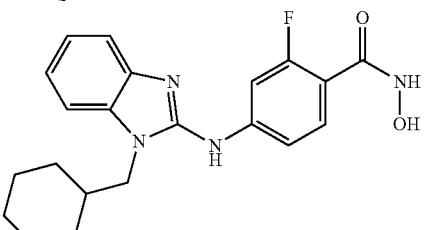
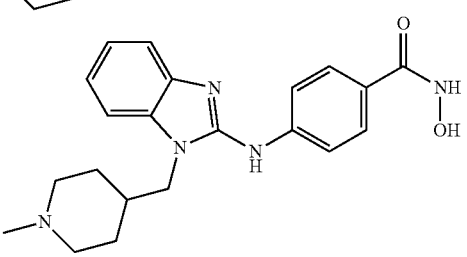

-continued

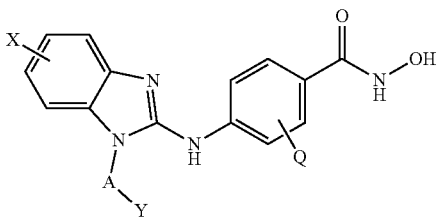

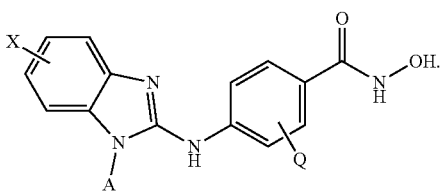

In certain aspects, the present invention is directed to compositions comprising a compound of formula (I):

and/or a compound of formula (II):

The group denoted by X may be any of H, halo, —$C_1$-$C_6$ alkyl, aryl, —$C_3$-$C_7$ cycloalkyl or -3- to 10-membered heterocycle, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

The groups denoted by A may be any of a bond, —$C_1$-$C_6$ alkyl, or —$C_3$-$C_7$ cycloalkyl, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

The group denoted by Y may be any of H, —$C_1$-$C_6$ alkyl, —$C_3$-$C_7$ cycloalkyl, aryl or -3- to 10-membered heterocycle any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

The group denoted by Q may be H, -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

A —$C_1$-$C_6$ alkyl group includes any straight or branched, saturated or unsaturated, substituted or unsubstituted hydrocarbon comprised of between one and six carbon atoms. Examples of —$C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —$C_1$-$C_6$ alkyl groups may include any applicable chemical moieties. Examples of groups that may be substituted onto any of the above listed —$C_1$-$C_6$ alkyl groups include but are not limited to the following examples: halo, —$C_1$-$C_6$ alkyl, —O—($C_1$-$C_6$ alkyl), —OH, —CN, —COOR', —OC(O)R', —NHR', N(R')$_2$, —NHC(O)R' or —C(O)NHR' groups. The groups denoted R' above may be —H or any —$C_1$-$C_6$ alkyl.

An aryl group includes any unsubstituted or substituted phenyl or napthyl group. Examples of groups that may be substituted onto ay aryl group include, but are not limited to: halo, —$C_1$-$C_6$ alkyl, —O—($C_1$-$C_6$ alkyl), —OH, —CN, —COOR', —OC(O)R', NHR', N(R') 2, —NHC(O), R', or —C(O)NEtR'. The group denoted R' may be —H or any —$C_1$-$C_6$ alkyl.

A $C_3$-$C_7$ cycloalkyl group includes any 3-, 4-, 5-, 6-, or 7-membered substituted or unsubstituted non-aromatic carbocyclic ring. Examples of $C_3$-$C_7$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1, 4-cyclohexadienyl, -1, 3-cycloheptadienyl, and -1,3,5-cycloheptatrienyl groups. Examples of groups that may be substituted onto $C_3$-$C_7$ cycloalkyl groups include, but are not limited to: -halo, —$C_1$-$C_6$ alkyl, —O—($C_1$-$C_6$ alkyl), —OH, —CN, —COOR', —OC(O) R', NHR', N(R')2, —NHC(O)R' or —C(O)NHR' groups. The groups denoted R' above include an —H or any unsubstituted —$C_1$-$C_6$ alkyl, examples of which are listed above.

Halo groups include any halogen. Examples include but are not limited to —F, —Cl, —Br, or —I.

A heterocycle may be any optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, suitable substituents include halogen, halogenated —$C_1$-$C_6$ alkyl, halogenated —$C_1$-$C_6$ alkoxy, amino, amidino, amido, azido, cyano, guanidino, hydroxyl, nitro, nitroso, urea, OS(O)$_2$R; OS(O)$_2$OR, S(O)$_2$OR S(O)$_{0-2}$R, C(O)OR wherein R may be H, $C_1$-$C_6$ alkyl, aryl or 3 to 10 membered heterocycle) OP(O)OR$_1$OR$_2$, P(O)OR$_1$OR$_2$, SO$_2$NR$_1$R$_2$, NR$_1$SO$_2$R$_2$ C(R$_1$)NR$_2$ C(R$_1$)NOR$_2$, R$_1$ and R$_2$ may be independently H, $C_1$-$C_6$ alkyl, aryl or 3 to 10 membered heterocycle), $NR_1C(O)R_2$, $NR_1C(O)OR_2$, $NR_3C(O)NR_2R_1$, $C(O)NR_1R_2$, $OC(O)NR_1R_2$. For these groups, $R_1$, $R_2$ and $R_3$ are each independently selected from H, $C_1$-$C_6$ alkyl, aryl or 3 to 10 membered heterocycle or $R_1$ and $R_2$ are taken together with the atoms to which they are attached to form a 3 to 10 membered heterocycle.

Possible substituents of heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl —S— (e.g., $CH_3S$, $C_2H_5S$), halogenated $C_{1-4}$ alkyl —S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl, and pyridopyrimidinyl groups.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Elements and acts in the example are intended to illustrate the invention for the sake of simplicity and have not necessarily been rendered according to any particular sequence or embodiment. The examples are also intended to establish possession of the invention by the Inventors.

Example 1: Anti-Metastatic Activity of a Composition Comprising ID#24 and an Anti-PD-1 Antibody Methods Six-week-old female balb/c mice were inoculated subcutaneously in the right flank with 0.1 mL of a 50% RPMI/50% Matrigel™ (BD Biosciences; Bedford, Mass.) mixture containing a suspension of 4T1-luc2 murine breast tumor cells (approximately $1\times10^6$ cells/mouse). 4T1-luc2 murine breast tumor cells are a line of luciferase expressing adenocarcinoma cell lines derived from mouse mammary gland stably transfected with firefly luciferase gene (luc2 vector) to produce intensified light. Accordingly, luciferase-induced luminescence may be a way of detecting these cells.

Eight days following inoculation, tumors were measured using a digital caliper. The calipers were used to measure width and length diameters of the tumor. The measured values were digitally recorded using animal study management software, Study Director V.2.1.1 (Study Log). Tumor volumes were calculated utilizing the formula:

$$\text{Tumor volume (mm}^3\text{)} = a \times \frac{b^2}{2},$$

where 'b' is the smallest diameter and 'a' is the largest diameter. Mice with tumor volumes of 306-519 mm³ were randomized into groups of 8 mice each by random equilibration so that each group has a Day 1 mean tumor volume (calculated using Study Director) of approximately 450 mm³. Tumor volumes were recorded when the mice were randomized and were taken three times weekly.

Treatments started on Day 1 of the experiment. Treatment with Compound ID #24 was given daily by oral gavage until the end of the study. Anti-mouse PD-1 (CD279, clone J43) (PD-1 inhibitor) antibody and anti-mouse CTLA4 (CD152, clone 9H10) (CTLA4 inhibitor) antibody were given intraperitoneally every other day for 8 days. The treatment groups in the experiment were:

Group 1: Compound ID #24 vehicle control (PO)+isotype control 0.25 mg/dose (IP)

Group 3: PD-1 inhibitor 0.25 mg/dose (IP)

Group 4: Compound ID #24 50 mg/kg (PO)+isotype control 0.25 mg/dose (IP)

Group 6: Compound ID #24 50 mg/kg (PO)+PD-1 inhibitor 0.25 mg/dose (IP)

Group 7: CTLA4 inhibitor 0.25 mg/dose (IP)+PD-1 inhibitor 0.25 mg/dose (IP)

Group 8: Compound ID #24 50 mg/kg (PO)+CTLA4 inhibitor 0.25 mg/dose (IP)+PD-1 inhibitor 0.25 mg/dose (IP).

When the control tumor reached a mean of ≥2300 mm³, mice were euthanized and lung tissue was collected and assessed for spontaneous lung metastases (detected by luminescence intensity). Mice were injected intraperitoneally with 150 mg/kg of luciferin thirty minute prior to euthanization. Lungs were placed in a luminometer and read for luminescence intensity.

Results

Figure 3:
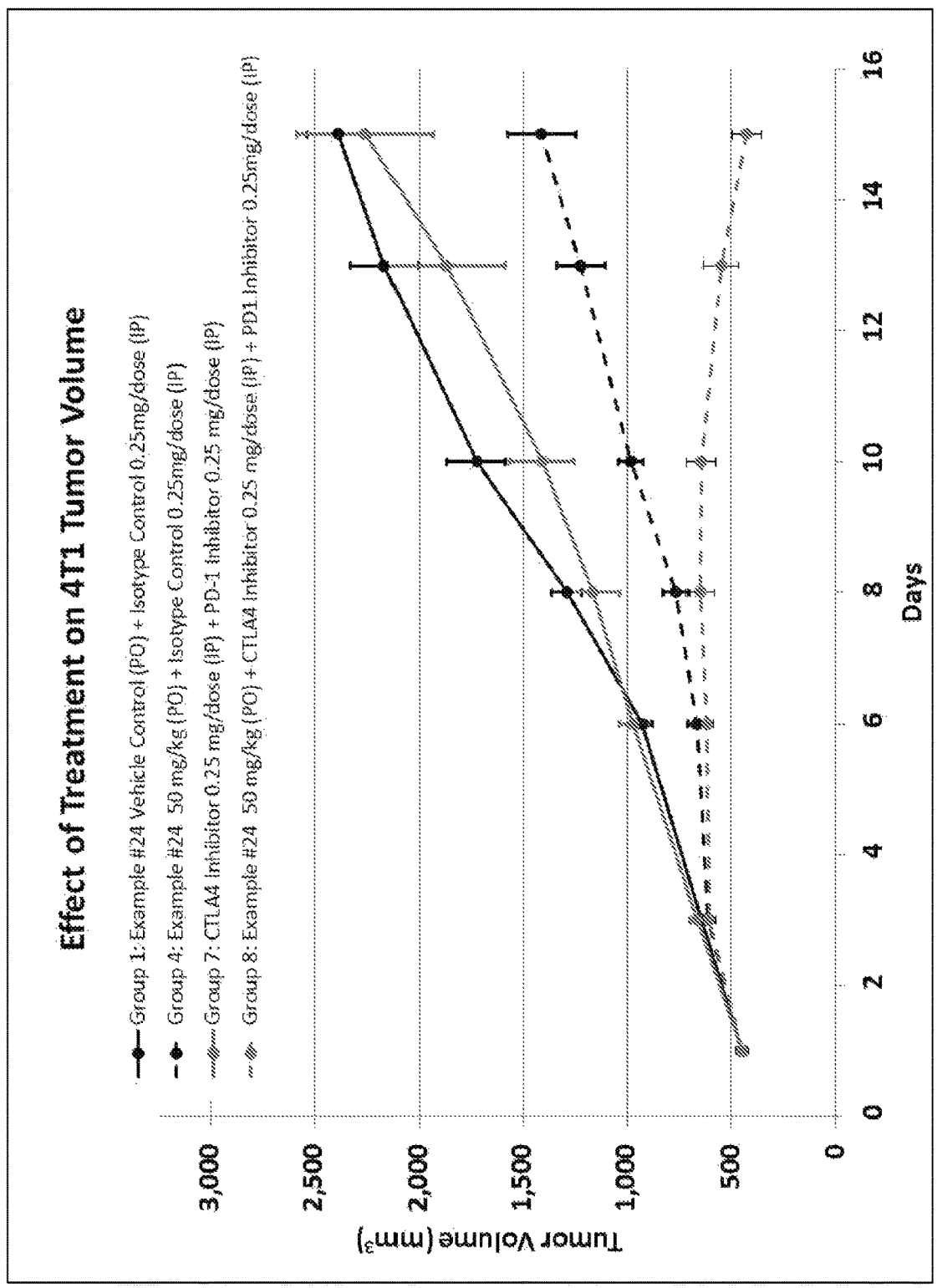
FIG. 3 depicts the effect of Compound ID #24 alone, a combination of a PD-1 axis binding antagonist and a CTLA4 antagonist, and a combination of all three therapeutic agents on 4T1 murine breast tumor volume growth.

As shown in FIGS. 1 and 3, the combination of the benzamide compound, compound ID #24, and the PD-1 inhibitor antibody produced a greater level of tumor cell growth inhibition than the individual treatments. Accordingly, the combination treatment of the PD-1 inhibitor and compound ID #24 has synergistic anti-cancer effects on 4T1 tumor cells.

Interestingly, as shown in FIG. 3, the addition of the CTLA4 inhibitor produced even greater synergistic results. The combination treatment of PD-1 inhibitor and the CTLA4 inhibitor impaired each inhibitor's inhibition of tumor growth, but the addition of compound ID #24 restored and enhanced the effectiveness of the tumor cell growth inhibition.

Figure 4:
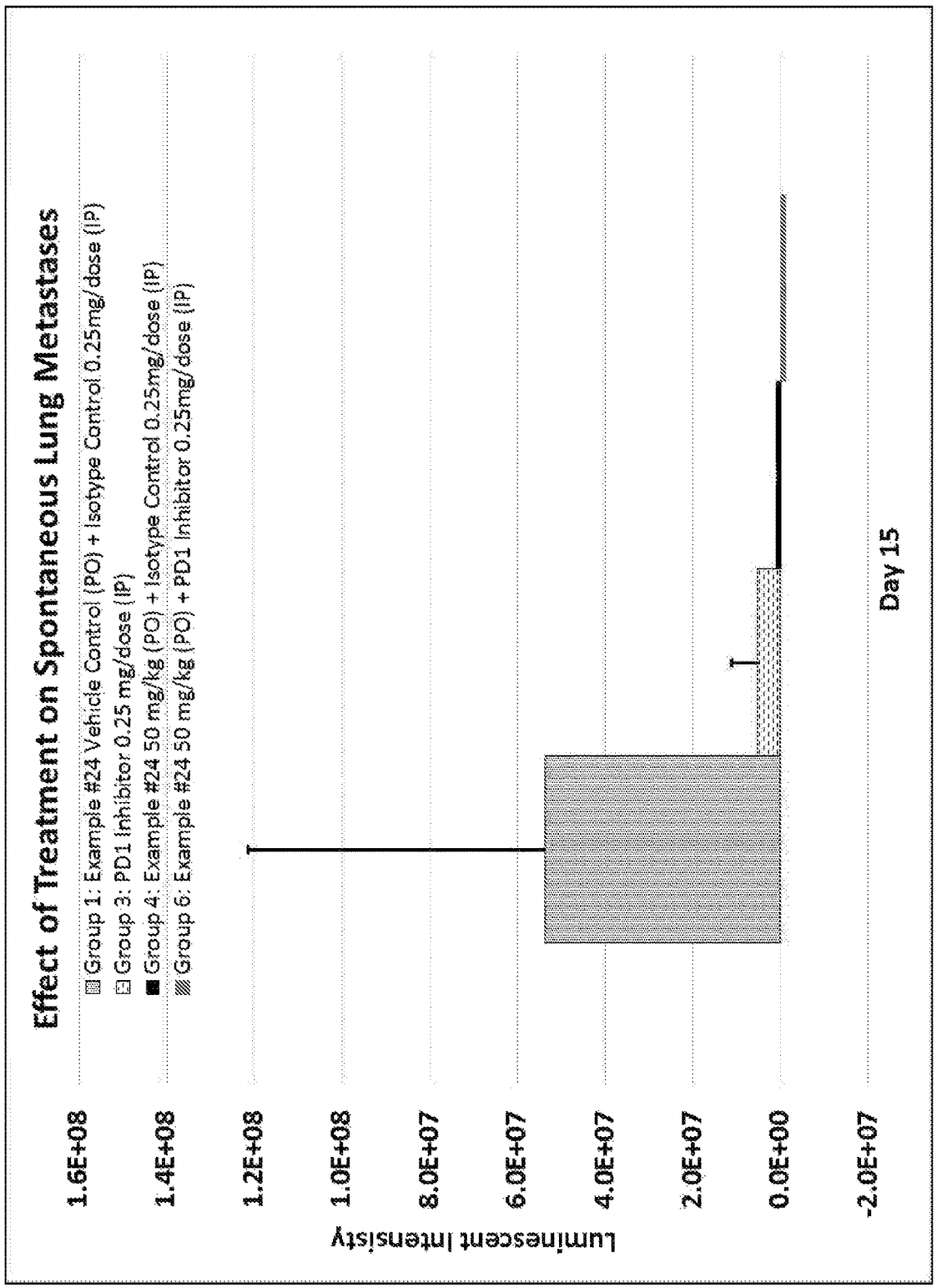
FIG. 4 depicts the effect of Compound ID #24 alone, a PD-1 axis binding antagonist alone, and a combination of the two therapeutic agents on the formation of spontaneous lung metastases from the transplantation of 4T1 murine breast tumor cells.
Figure 6:
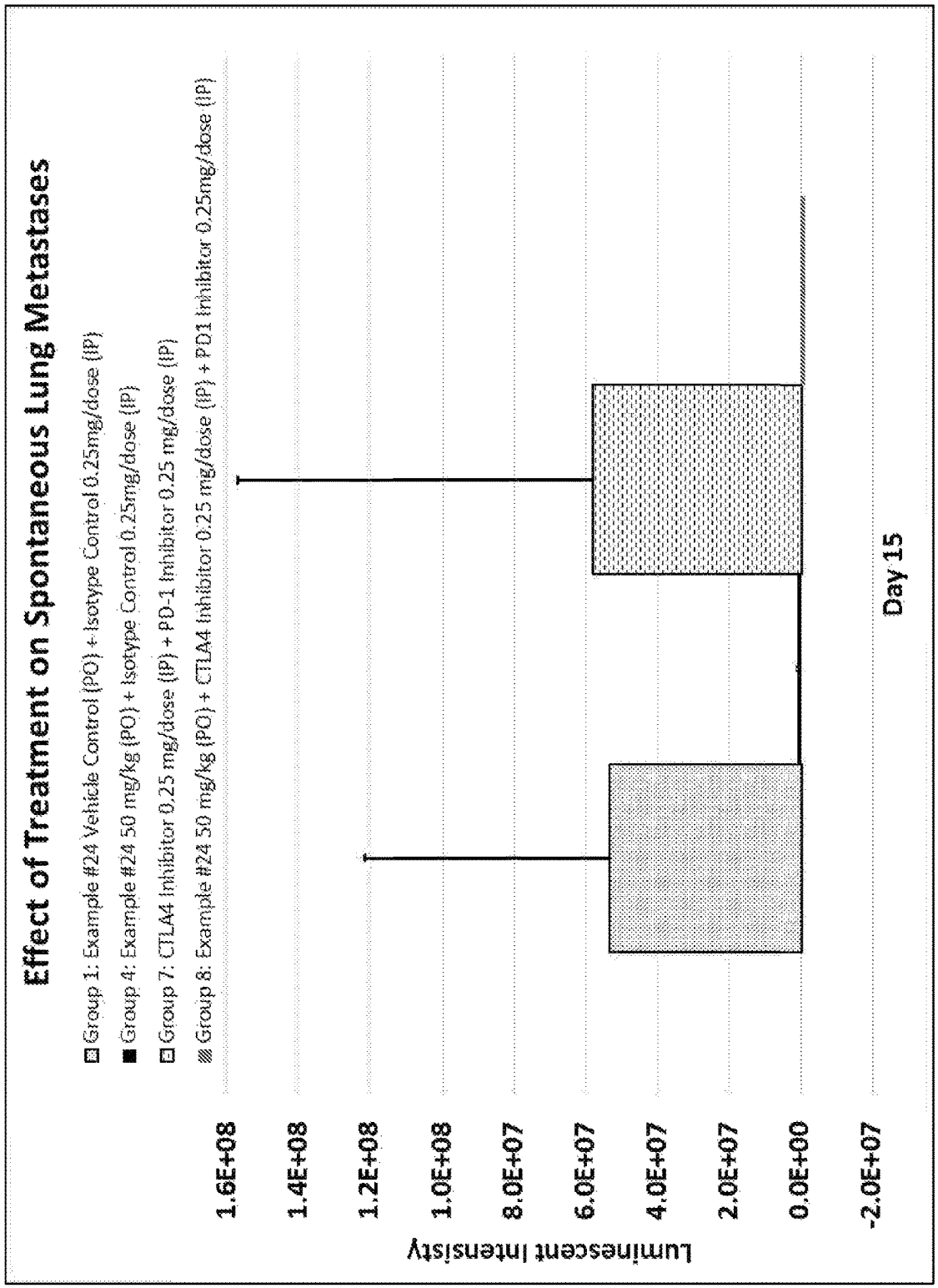
FIG. 6 depicts the effect of Compound ID #24 alone, a combination of a PD-1 axis binding antagonist and a CTLA4 antagonist, and a combination of all three therapeutic agents on the formation of spontaneous lung metastases from the transplantation of 4T1 murine breast tumor cells.

Similar synergy results were observed in evaluating the effect of the various treatments on the presence of spontaneous lung metastasis (see FIGS. 4 and 6). Thus the combination of the benzamide compound, compound ID #24, and the PD-1 inhibitor have synergistic properties in inhibiting tumor cell metastasis (FIG. 4).

The combination of compound ID #24, the PD-1 inhibitor, and the CTLA4 inhibitor also produces synergistic inhibition of tumor cell metastatic (FIG. 6).

Example 2: Anti-Tumor Cell Growth and Anti-Metastatic Activity of a Composition Comprising ID#24 and a CTLA4 Inhibitor Methods Six-week-old female balb/c mice were inoculated subcutaneously in the right flank with 0.1 mL of a 50% RPMI/50% Matrigel™ (BD Biosciences; Bedford, Mass.) mixture containing a suspension of 4T1-luc2 murine breast tumor cells (approximately $1\times10^6$ cells/mouse). 4T1-luc2 murine breast tumor cells are a line of luciferase expressing adenocarcinoma cell lines derived from mouse mammary gland stably transfected with firefly luciferase gene (luc2 vector) to produce intensified light. Accordingly, luciferase-induced luminescence may be a way of detecting these cells.

Eight days following inoculation, tumors were measured using a digital caliper. The calipers were used to measure width and length diameters of the tumor. The measured values were digitally recorded using animal study management software, Study Director V.2.1.1 (Study Log). Tumor volumes were calculated utilizing the formula:

$$\text{Tumor volume (mm}^3\text{)} = a \times \frac{b^2}{2},$$

where 'b' is the smallest diameter and 'a' is the largest diameter. Mice with tumor volumes of 306-519 mm³ were randomized into groups of 8 mice each by random equilibration so that each group has a Day 1 mean tumor volume (calculated using Study Director) of approximately 450 mm³. Tumor volumes were recorded when the mice were randomized and were taken three times weekly.

Treatments started on Day 1 of the experiment. Treatment with Compound ID #24 was given daily by oral gavage until the end of the study. Anti-mouse CTLA4 (CD152, clone $9H_{10}$) (CTLA4 inhibitor) antibody and anti-mouse PD1 (CD279, clone J43) (PD1 inhibitor) antibody were given intraperitoneally every other day for 8 days. The treatment groups in the experiment were:

Group 1: Compound ID #24 vehicle control (PO)+isotype control 0.25 mg/dose (IP)
Group 2: CTLA inhibitor 0.25 mg/dose (IP)
Group 4: Compound ID #24 50 mg/kg (PO)+isotype control 0.25 mg/dose (IP)
Group 5: Compound ID #24 50 mg/kg (PO)+CTLA4 inhibitor 0.25 mg/dose (IP)
Group 7: CTLA inhibitor 0.25 mg/dose (IP)+PD1 inhibitor 0.25 mg/dose (IP)
Group 8: Compound ID #24 50 mg/kg (PO)+CTLA4 inhibitor 0.25 mg/dose (IP)+PD1 inhibitor 0.25 mg/dose (IP).

When the control tumor reached a mean of ≥2300 mm³, mice were euthanized and lung tissue was collected and assessed for spontaneous lung metastases (detected by luminescence intensity). Mice were injected intraperitoneally with 150 mg/kg of luciferin thirty minutes prior to euthanization. Lungs were placed in a luminometer and read for luminescence intensity.

Results

Figure 2:
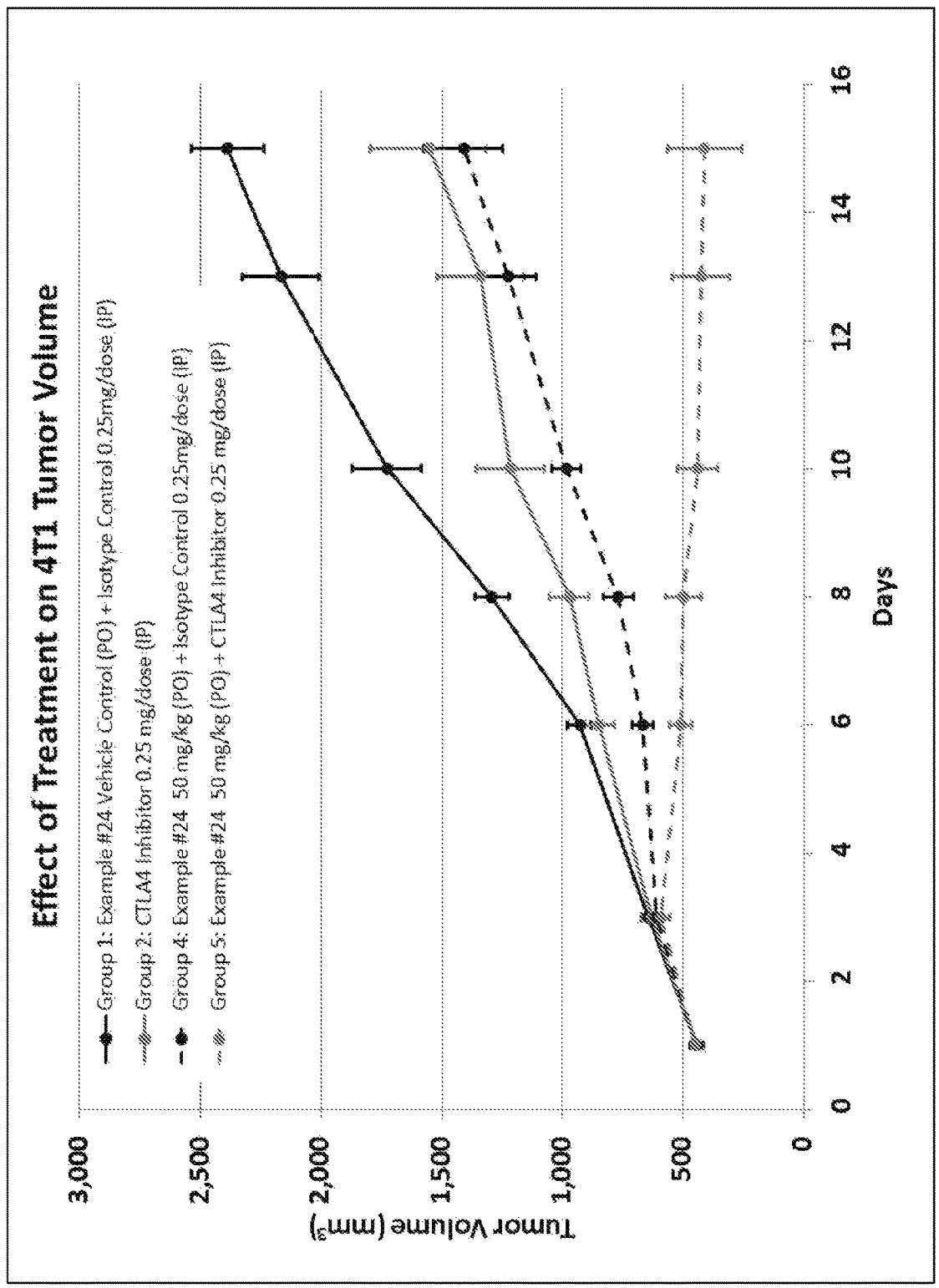
FIG. 2 depicts the effect of Compound ID #24 alone, a CTLA4 antagonist alone, and a combination of the two therapeutic agents on 4T1 murine breast tumor volume growth.

As shown in FIG. 2, the combination of the benzamide compound, compound ID #24, and a CTLA4 inhibitor antibody produced a greater level of tumor cell growth inhibition than the individual treatments. Accordingly, the combination treatment of the CTLA4 inhibitor and compound ID #24 has synergistic anti-cancer effects on 4T1 tumor cells. Interestingly, as shown in FIG. 3, the addition of the PD1 inhibitor produced even greater synergistic results. The combination treatment of CTLA4 inhibitor and the PD1 inhibitor impaired each inhibitor's inhibition of tumor growth, but the addition of compound ID #24 restore and enhanced the effectiveness of the tumor cell growth inhibition (FIG. 3).

Figure 5:
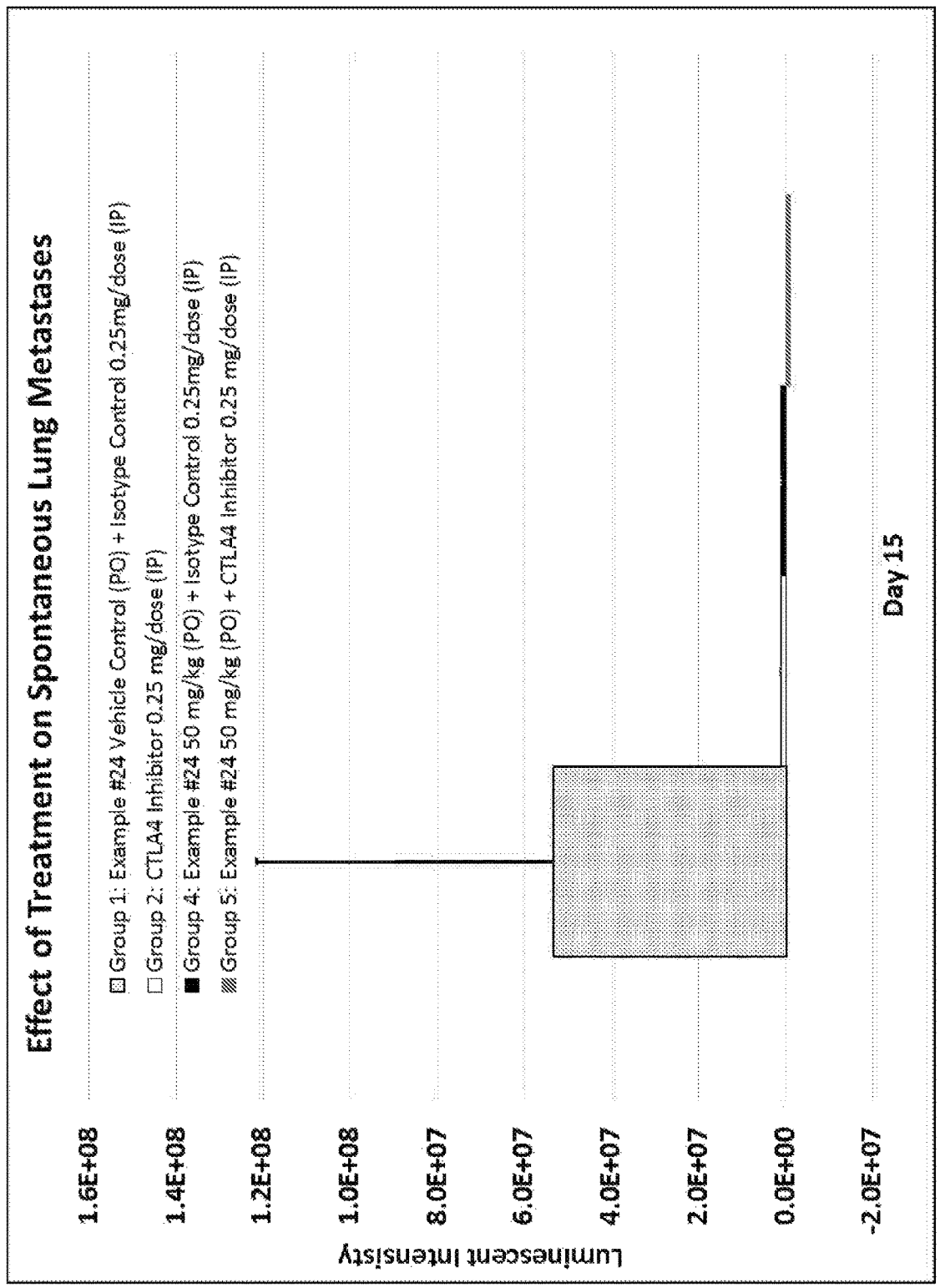
FIG. 5 depicts the effect of Compound ID #24 alone, a CTLA4 antagonist alone, and a combination of the two therapeutic agents on the formation of spontaneous lung metastases from the transplantation of 4T1 murine breast tumor cells.

Similar synergy results were observed in evaluating the effect of the various treatments on the presence of spontaneous lung metastasis (see FIGS. 5-6). Thus the combination of the benzamide compound, compound ID #24, and the CTLA4 inhibitor have synergistic properties in inhibiting tumor cell metastasis (FIG. 5).

The combination of compound ID #24, the CTLA4 inhibitor, and the PD1 inhibitor also produces synergistic inhibition of tumor cell metastatic.

Example 3: Effect of Benzamide Compounds on Cell Viability

Cell viability in the presence of varying concentrations of the benzamide compounds at different time points was used to assess cytotoxicity and the effect of the compounds on cell proliferation. $IC_{50}$ (or percent activity) data for the benzamide compounds in the human acute leukemia cell line (HL-60) is summarized in Table 2.

TABLE 2

Single Agent Growth Inhibitory Results

| Compound | $IC_{50}$ (μM) |
| --- | --- |
| ID#24 | 1.15 |
| ID#25 | 3.90 |
| ID#26 | 0.66 |

Cell Viability Assay—Cell viability was measured by the CellTiter-Glo® cell viability assay Promega (Madison, Wis.). The CellTiter-Glo® Luminescent Cell Viability Assay is a homogeneous method to determine the number of viable cells in culture based on quantitation of the ATP present, which signals the presence of metabolically active cells. Following treatment, CellTiter-Glo® is added to treatment wells and incubated at 37° C. luminescence values were measured at using a Molecular Devices Spectramax microplate reader.

Single Agent Studies—Cells were grown to 70% confluency, trypsinized, counted, and seeded in 96 well flat-bottom plates at a final concentration of $2.5\times10^3$-$5\times10^3$ cells/well (Day 0). Cells were allowed to incubate in growth media for 24 hours to allow for maximum adhesion. Treatment with the test agents or standard agents began on Day 1 and continued for 72 hours. At the 72-hour time point, treatment containing media was removed. Viable cell numbers are quantified by the CellTiter-Glo® cell viability assay as described above. Experiments were run with triplicate concentrations to determine growth inhibitory activity. Results from these studies were used to calculate an IC50 value (concentration of drug that inhibits cell growth by 50 percent of control) for each compound.

Data Collection—For single agent and combination studies, data from each experiment was collected and expressed as % Cell Growth using the following calculation:

% Cell Growth=$(f_{test}/f_{vehicle}) \times 100$

Where $f_{test}$ is the luminescence of the tested sample, and $f_{vehicle}$ is the luminescence of the vehicle in which the drug is dissolved. Dose response graphs and $IC_{50}$ values were generated using Prism 6 software (GraphPad).

Example 4: Synergism

To test for synergy between the benzamide compound and DNA methyltransferase inhibitors, the $IC_{50}$ of different benzamide compound of the invention in combination with 5-azacytidine against HL-60 cells was evaluated.

For each experiment, the CI value at the $ED_{50}$, $ED_{75}$, $ED_{90}$ and $ED_{95}$ (dose of drug combination that produces an effect, e.g. reduction of cell proliferation of 50%, 75%, 90% and 95%) was calculated for drug combination. The synergism factors (CI values) for the various combinations are summarized in Table 3 below. The CI values have been calculated using the program CompuSyn (CompuSyn, Paramus, N.J.). The CI values were <0.90, showing synergy between the benzamide compound and a DNA methyltransferase inhibitor.

TABLE 3

CI Values in combination with 5-azacytidine at respective ED concentrations:

| ID#24 and 5-Azacytidine | | ID#25 and 5-Azacytidine | | ID#26 and 5-Azacytidine | |
|---|---|---|---|---|---|
| $EC_x$ | CI | $EC_x$ | CI | $EC_x$ | CI |
| 0.50 | 0.88239 | 0.50 | 0.7185 | 0.50 | 0.20006 |
| 0.75 | 0.83776 | 0.75 | 0.68446 | 0.75 | 0.1749 |
| 0.90 | 0.79553 | 0.90 | 0.65234 | 0.90 | 0.15342 |
| 0.95 | 0.76811 | 0.95 | 0.63152 | 0.95 | 0.14046 |

REFERENCES

1. Lafferty et al., *Aust. J. Exp. Biol. Med. ScL* 53: 27-42 (1975).
2. Bretscher et al., Science 169: 1042-1049 (1970)
3. Bretscher, P. A., P.N.A.S. USA 96: 185-190 (1999)
4. Jenkins et al, J. Exp. Med. 165: 302-319 (1987).
5. Lenschow et al., Ann. Rev. Immunol. 14:233 (1996).
6. Okazaki T et al., Intern. Immun. 19(7):813 (2007).
7. Thompson R H et al., Cancer Res 66(7):3381 (2006).
8. Ahmadzadeh et al., Blood 114(8):1537 (2009).
9. Sharpe et al., Nat Rev 2002.
10. Keir M E et al., 2008 Annu. Rev. Immunol. 26:677.
11. Long, B. H. et al., *Cancer Res.,* 51:5275-5284 (1991).
12. Giannakakou, P. et al., J. Biol. Chem., 272(27):17118-17125 (1997).
13. Riss, T. L. et al., Mol. Biol. Cell, 3(Suppl.):184a (1992).
14. Stephens, T. C. et al., "The evaluation of combinations of cytotoxic drugs and radiation: Isobolograms and therapeutic synergism", *Rodent Tumor Models in Experimental Cancer Therapy*, p. 248. Pergamon Press, NY, publ., Kallman, R. F., ed.
15. Long, B. H., Cancer Res., 54(16):4355-4361 (1994).
16. Williams, R. C. et al., Meth. Enzymol., 85(Pt. D):376-385 (1982).
17. Gehan, G. A., "Biometrika, 52:203-233 (1985).
18. Walunas, T. L. et al., Immunity, 1(5):405-413 (August 1994).
19. Linsley, P. S. et al., J. Exp. Med., 173:721-730 (1991).
20. Linsley, P. S. et al., J. Exp. Med., 174:561-569 (1991).
21. Brunet, J. F. et al., Nature, 328:267-270 (1987).
22. Gross, J. A. et al., J. Immunol., 149:380-388 (1992).
23. Alegre, M. L. et al., Nat. Rev. Immunol., 1:220-228 (2002).
24. Lindsten, T. et al., J. Immunol., 151:3489-3499 (1993).
25. Walunas, T. L. et al., Immunity, 1:405-413 (1994).
26. Linsley, P. S. et al., Immunity, 1:793-801 (1994).
27. Walunas, T. L. et al., J. Exp. Med., 183:2541-2550 (1996).
28. Krummel, M. F. et al., J. Exp. Med., 183:2533-2540 (1996).
29. Brunner, M. C. et al., J. Immunol., 162:5813-5820 (1999).
30. Greenwald, R. J. et al., Eur. J. Immunol., 32:366-373 (2002).
31. Leach, D. R. et al., Science, 271:1734-1736 (1996).
32. van Elsas, A. et al., J. Exp. Med., 190:355-366 (1999).
33. van Elsas, A. et al., J. Exp. Med., 194:481-489 (2001).
34. Hurwitz, A. A. et al., Cancer Res., 60:2444-2448 (2000).
35. Robbins and Angell, 1976, *Basic Pathology*, 2d Ed., W. B. Saunders Co., Philadelphia.
36. Bulinski, J. Cell Sci., 110:3055-3064 (1997).
37. Panda, Proc. Natl. Acad. Sci. USA, 94:10560-10564 (1997).
38. Muhlradt, Cancer Res., 57:3344-3346 (1997).
39. Nicolaou, Nature, 387:268-272 (1997).
40. Vasquez, Mol. Biol. Cell., 8:973-985 (1997).
41. Panda, J. Biol. Chem., 271:29807-29812 (1996).
42. Schwartz, R. H., Science, 248:1349-1356 (1990).

What is claimed is:

1. A composition comprising:
An antibody against PD-1, wherein the antibody against PD-1 is a PD-1 axis binding antagonist; and
A compound selected from the group consisting of 4-(1-(cyclohexylmethyl)-1H-benzo[d]imidazole-2-ylamino)-N-hydroxybenzamide, 4-(1-cyclohexyl-1H-benzo[d]imidazole-2-ylamino)-N-hydroxybenzamide and 4-(1-cycloheptyl-1H-benzo[d]imidazole-2-ylamino)-N-hydroxybenzamide.

2. The composition of claim 1, wherein the compound is 4-(1-(cyclohexylmethyl)-1H-benzo[d]imidazol-2-ylamino)-N-hydroxybenzamide.

3. The composition of claim 1, wherein the compound is 4-(1-cyclohexyl-1H-benzo[d]imidazol-2-ylamino)-N-hydroxybenzamide.

4. The composition of claim 1, further comprising an antibody against PD-L1.

5. The composition of claim 1, wherein the antibody against PD-1 comprises a heavy chain variable region having the sequence set forth in SEQ ID NO:22 and a light chain variable region having a sequence set forth in SEQ ID NO:19.

6. The composition of claim 1, wherein the compound is 4-(1-cycloheptyl-1H-benzo[d]imidazol-2-ylamino)-N-hydroxybenzamide.

7. The composition of claim 1, further comprising a CTLA4 antagonist selected from the group consisting of: CTLA4 inhibitors that agonize the co-stimulatory pathway, CD28 inhibitors that disrupts the ability of CD8 to bind to its cognate ligand, B7 inhibitors that disrupt the ability of B7 to bind to CD28 and/or CTLA4, CD80 inhibitors that disrupt the ability of CD80 to bind to CD28 and/or CTLA4, and CD86 inhibitors that disrupt the ability of CD80 to bind to CD28 and/or CTLA4.

8. The composition of claim 7, wherein the CTLA4 antagonist is selected from the group consisting of: a small molecule inhibitor of CD28, a small molecule inhibitor of CD80; a small molecule inhibitor of CD86; a small molecule inhibitor of CTLA4; an antisense molecule directed against CD28; an antisense molecule directed against CD80; an antisense molecule directed against CD86; an antisense molecule directed against CTLA4; an adnectin directed against CD28; an adnectin directed against CD80; an adnectin directed against CD86; an adnectin directed against CTLA4; a single-stranded RNA interference inhibitor of CD28; a single-stranded RNA interference inhibitor of CD80; a single-stranded RNA interference inhibitor of CD86; a single-stranded RNA interference inhibitor of CTLA4; a double-stranded RNA interference inhibitor of CD82; a double-stranded RNA interference inhibitor of CD80; a double-stranded RNA interference inhibitor of CD86, a double-stranded RNA interference inhibitor of CTLA4; an antibody directed to CD28; an antibody directed to CD80; an antibody directed to CD86; and an antibody directed to CTLA4.

9. The composition of claim 8, wherein the antibody directed to CTLA4 is selected from the group consisting of: ipilimumab and tremelimumab.

10. The composition of claim 7, further comprising a peptide antigen.

11. The composition of claim 10, wherein the peptide antigen is gp100.

12. The composition of claim 7, further comprising an anti-proliferative cytotoxic agent selected from the group consisting of an alkylating agent, an antimetabolite, vinca alkaloids, antitumor antibiotics, enzymes, lymphokines, epipodophyllotoxins, navelbene, CPT-11, anastrazole, letrazole, capecitabine, reloxafine, cyclophosphamide, ifosamide, and droloxafine.

13. The composition of claim 12, wherein the alkylating agent is selected from the group consisting of: nitrogen mustards, ethylenimine derivatives, alkyl sulfonates, nitrosoureas, and triazenes.

14. The composition of claim 12, wherein the antimetabolite is selected from the group consisting of: folic acid antagonists, pyrimidine analogs, purine analogs, and adenosine deaminase inhibitors.

15. The composition of claim 1, further comprising a DNA demethylating agent, and the DNA demethylating agent is a DNA methyltransferase inhibitor.

16. The composition of claim 15, wherein the DNA methyltransferase inhibitor is a cytidine analog.

17. The composition of claim 16, wherein the cytidine analog is selected from the group consisting of azacitidine and decitabine.

* * * * *

SEQUENCE LISTING

```
<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1
```

```
Gly Phe Thr Phe Ser Xaa Ser Trp Ile His
1               5                   10
```

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 2

```
Ala Trp Ile Xaa Pro Tyr Gly Gly Ser Xaa Tyr Tyr Ala Asp Ser Val
1               5                   10                  15

Lys Gly
```

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

```
Arg His Trp Pro Gly Gly Phe Asp Tyr
1               5
```

<210> SEQ ID NO 4
<211> LENGTH: 25
<212> TYPE: PRT
<213> ORGANISM: Artificial Sequence
<220> FEATURE:
<223> OTHER INFORMATION: Synthetic peptide

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide

<400> SEQUENCE: 5

```
Trp Val Arg Gln Ala Pro Gly Lys Gly Leu Glu Trp Val
1               5                   10
```

<210> SEQ ID NO 6
<211> LENGTH: 32
<212> TYPE: PRT
<213> ORGANISM: Artificial Sequence
<220> FEATURE:
<223> OTHER INFORMATION: Synthetic peptide

<400> SEQUENCE: 6

```
Arg Phe Thr Ile Ser Ala Asp Thr Ser Lys Asn Thr Ala Tyr Leu Gln
```

```
                1               5                  10                  15
            Met Asn Ser Leu Arg Ala Glu Asp Thr Ala Val Tyr Tyr Cys Ala Arg
                                20                  25                  30
```

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

```
Trp Gly Gln Gly Thr Leu Val Thr Val Ser Ala
 1               5                  10
```

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 8

```
Arg Ala Ser Gln Xaa Xaa Xaa Thr Xaa Xaa Ala
 1               5                  10
```

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

```
Ser Ala Ser Xaa Leu Xaa Ser
 1               5
```

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Gln Gln Xaa Xaa Xaa Xaa Pro Xaa Thr

<210> SEQ ID NO 11
<211> LENGTH: 23
<212> TYPE: PRT
<213> ORGANISM: Artificial sequence
<220> FEATURE:
<223> OTHER INFORMATION: Synthetic peptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Phe Gly Gln Gly Thr Lys Val Glu Ile Lys Arg
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ile Met Asp Gln Val Pro Phe Ser Val
1               5

<210> SEQ ID NO 16
<211> LENGTH: 9
<212> TYPE: PRT
<213> ORGANISM: Artificial Sequence
<220> FEATURE:

<223> OTHER INFORMATION: Synthetic peptide

<400> SEQUENCE: 16

Tyr Leu Glu Pro Gly Pro Val Thr Val
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide

<400> SEQUENCE: 17

Trp Gly Gln Gly Thr Leu Val Thr Val Ser Ser
1               5                   10

<210> SEQ ID NO 18
<211> LENGTH: 108
<212> TYPE: PRT
<213> ORGANISM: Artificial Sequence
<220> FEATURE:
<223> OTHER INFORMATION: Synthetic peptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 19
<211> LENGTH: 214
<212> TYPE: PRT
<213> ORGANISM: Artificial Sequence
<220> FEATURE:
<223> OTHER INFORMATION: Synthetic peptide

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 20
<211> LENGTH: 214
<212> TYPE: PRT
<213> ORGANISM: Artificial Sequence
<220> FEATURE:
<223> OTHER INFORMATION: Synthetic peptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 118

<212> TYPE: PRT
<213> ORGANISM: Artificial Sequence
<220> FEATURE:
<223> OTHER INFORMATION: Synthetic peptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 22
<211> LENGTH: 440
<212> TYPE: PRT
<213> ORGANISM: Artificial Sequence
<220> FEATURE:
<223> OTHER INFORMATION: Synthetic peptide

<400> SEQUENCE: 22

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 23
<211> LENGTH: 118
<212> TYPE: PRT
<213> ORGANISM: Artificial Sequence
<220> FEATURE:
<223> OTHER INFORMATION: Synthetic peptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 24
<211> LENGTH: 448
<212> TYPE: PRT
<213> ORGANISM: Artificial Sequence
<220> FEATURE:
<223> OTHER INFORMATION: Synthetic peptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395                 400

Ser Asp Gly Ser Phe Phe Leu Tyr Ser Lys Leu Thr Val Asp Lys Ser
            405             410                 415

Arg Trp Gln Gln Gly Asn Val Phe Ser Cys Ser Val Met His Glu Ala
        420             425             430

Leu His Asn His Tyr Thr Gln Lys Ser Leu Ser Leu Ser Pro Gly Lys
        435             440             445
```